United States Patent
Aravamudan

(10) Patent No.: US 12,329,463 B1
(45) Date of Patent: Jun. 17, 2025

(54) SYSTEM AND METHOD FOR VISUALIZATION OF VECTORCARDIOGRAMS FOR ABLATION PROCEDURES

(71) Applicant: Anumana, Inc., Cambridge, MA (US)

(72) Inventor: Murali Aravamudan, Andover, MA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/405,656

(22) Filed: Jan. 5, 2024

(51) Int. Cl.
*A61B 34/10* (2016.01)
*A61B 5/341* (2021.01)
*A61B 5/346* (2021.01)
*A61B 18/00* (2006.01)

(52) U.S. Cl.
CPC .............. *A61B 34/10* (2016.02); *A61B 5/341* (2021.01); *A61B 5/346* (2021.01); *A61B 2018/00351* (2013.01); *A61B 2018/00577* (2013.01); *A61B 2034/104* (2016.02)

(58) Field of Classification Search
CPC ................................ A61B 34/10; A61B 5/341
USPC ........................................................ 600/512
See application file for complete search history.

(56) References Cited

U.S. PATENT DOCUMENTS

| 11,065,060 | B2 | 7/2021 | Villongco et al. |
| 2011/0184300 | A1 | 7/2011 | Shvilkin et al. |
| 2015/0238101 | A1* | 8/2015 | Weng ................... A61N 1/3987 600/512 |
| 2017/0209698 | A1* | 7/2017 | Villongco .............. G16H 50/50 |
| 2020/0405393 | A1* | 12/2020 | Villongco ............ A61N 1/3706 |

FOREIGN PATENT DOCUMENTS

WO     2019210090 A1    10/2019

OTHER PUBLICATIONS

Pastore et al; Applicability of the Electro-Vectorcardiogram in Current Clinical Practice; Arq Bras Cardiol. Jul. 2019; 113(1): 87-99.

* cited by examiner

*Primary Examiner* — Ronald Hupczey, Jr.
(74) *Attorney, Agent, or Firm* — Caldwell Intellectual Property Law

(57) ABSTRACT

A system for visualization of vectorcardiograms for ablation procedures, the system including at least a processor and a memory communicatively connected to the at least a processor, the memory containing instructions configuring the at least a processor to receive an input matrix having a plurality of electrocardiogram signals associated with a plurality of time variables, transform the plurality of electrocardiogram signals into a cardiac vector as a function of the input matrix, and determine at least one ablative reaction as a function of the cardiac vector, wherein determining the at least one ablative reaction includes generating a graphical visualization of an X-Y plot, wherein cardiac deviations are plotted along a vertical axis of the X-Y plot and time variables are plotted along a horizontal axis of the X-Y plot.

16 Claims, 13 Drawing Sheets

SYSTEM AND METHOD FOR VISUALIZATION OF VECTORCARDIOGRAMS FOR ABLATION PROCEDURES

FIELD OF THE INVENTION

The present invention generally relates to the field of transformed visualization of an electrocardiogram. In particular, the present invention is directed to an apparatus and a method for visualization of vectorcardiograms for ablation procedures.

BACKGROUND

Improvements in heart monitoring have been lackluster. Instead, current systems continue to rely on old and outdated processes to provide interpretation of electrocardiogram (ECG) signals. Current systems utilized for ablation procedures continue to interpret ECG signals thorough manual analysis by trained healthcare professionals. These systems can be time-consuming and subject to inter-observer variability. In addition, these systems cannot provide immediate and/or informative feedback for use during the procedures.

SUMMARY OF THE DISCLOSURE

In an aspect, a system for visualization of vectorcardiograms for ablation procedures is described. The system includes at least a processor and a memory communicatively connected to the at least a processor. The memory contains instructions configuring the at least a processor to receive an input matrix having a plurality of electrocardiogram signals associated with a plurality of time variables, wherein the plurality of electrocardiogram signals is generated using at least one sensor of a plurality of sensors connected to a patient during an ablation procedure. The processor is further configured to transform the plurality of electrocardiogram signals into a cardiac vector as a function of the input matrix, and determine at least one ablative reaction for the vectorcardiogram image as a function of the cardiac vector, wherein determining the at least one ablative reaction includes generating a graphical visualization of an X-Y plot, wherein cardiac deviations are plotted along a vertical axis of the X-Y plot and time variables are plotted along a horizontal axis of the X-Y plot.

In another aspect, a method for visualization of vectorcardiograms for ablation procedures is described. The method includes receiving, by at least a processor, an input matrix comprising a plurality of electrocardiogram signals associated with a plurality of time variables, wherein the plurality of electrocardiogram signals is generated using at least one sensor of a plurality of sensors connected to a patient during an ablation procedure. The method further includes transforming, by the at least a processor, the plurality of electrocardiogram signals into a cardiac vector as a function of the input matrix. The method further includes determining, by the at least a processor, at least one ablative reaction as a function of the cardiac vector, wherein determining the at least one ablative reaction includes generating a graphical visualization of an X-Y plot, wherein cardiac deviations are plotted along a vertical axis of the X-Y plot and time variables are plotted along a horizontal axis of the X-Y plot.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for visualization of vectorcardiograms during ablation procedures. In an embodiment, system includes a computing device configured to receive an input matrix having a plurality of electrocardiogram signals associated with a plurality of time variables, wherein the plurality of electrocardiogram signals is generated using at least one sensor of a plurality of sensors connected to a patient during an ablation procedure. The computing device is further configured to transform the plurality of electrocardiogram signals into a cardiac vector as a function of the input matrix, generate a vectorcardiogram image as a function of the cardiac vector, wherein the vectorcardiogram image comprises a representation of the cardiac vector in a three-dimensional (3D) space and determine at least one ablative reaction for the vectorcardiogram image.

Aspects of the present disclosure can be used to generate vectorcardiogram images and/or ablative reactions during ablative procedures. Aspects of the present disclosure can further be used to iteratively train machine learning models utilized for ablative procedures. This is so, at least in part by comparing images and associated outputs. Exemplary embodiments illustrating aspects of the present disclosure are described below in the context of several specific examples.

Figure 1:
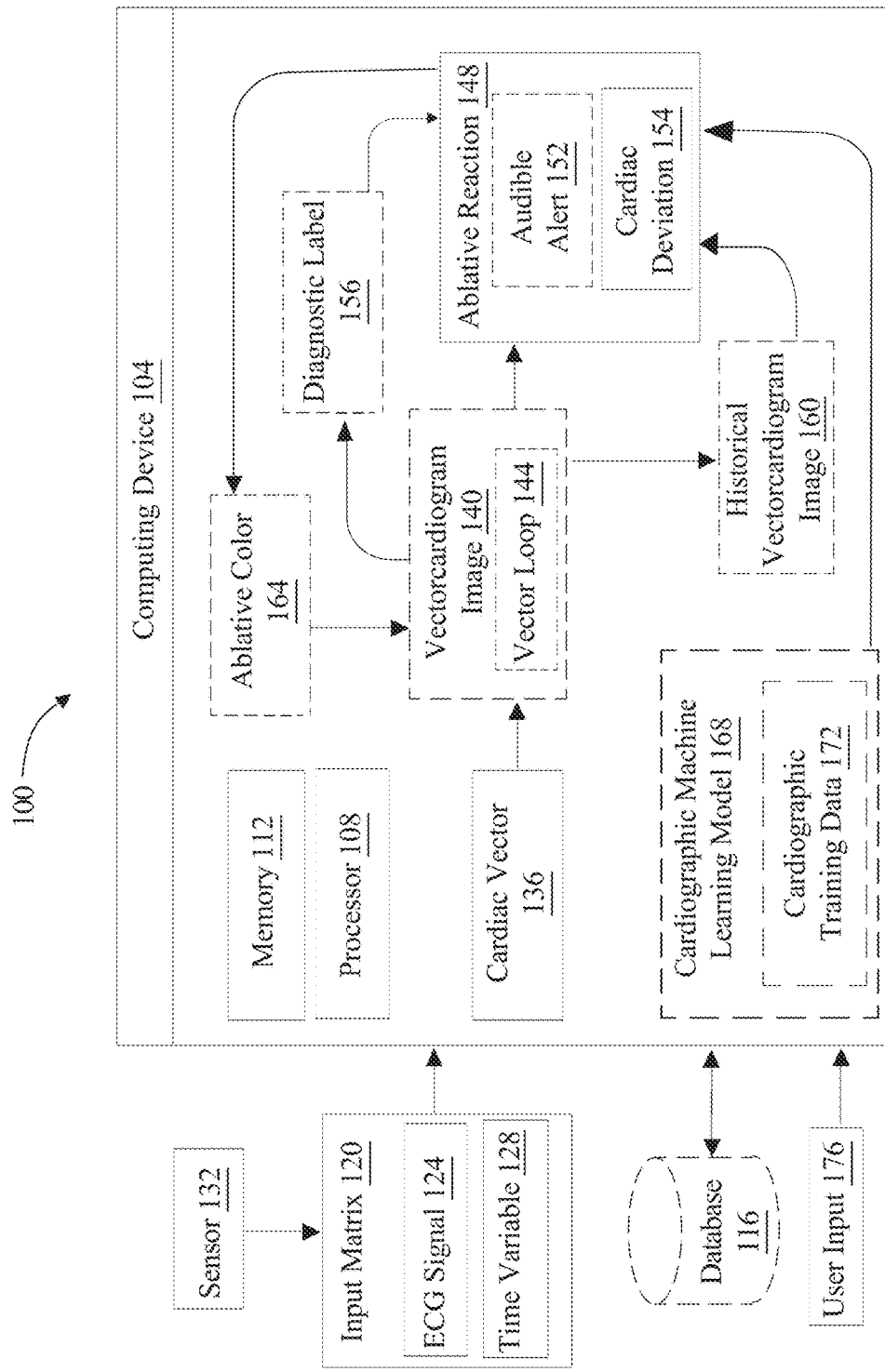
FIG. 1 is a block diagram of a system for visualization of vectorcardiograms for ablation procedures.

Referring now to FIG. 1, a system 100 for visualization of vectorcardiograms for ablation procedures is described. System 100 includes a computing device 104. System 100 includes a processor 108. Processor 108 may include, without limitation, any processor 108 described in this disclosure. Processor 108 may be included in a and/or consistent with computing device 104. In one or more embodiments, processor 108 may include a multi-core processor. In one or more embodiments, multi-core processor may include multiple processor cores and/or individual processing units. "Processing unit" for the purposes of this disclosure is a device that is capable of executing instructions and performing calculations for a computing device 104. In one or more embodiments, processing units may retrieve instructions from a memory, decode the data, secure functions and transmit the functions back to the memory. In one or more embodiments, processing units may include an arithmetic logic unit (ALU) wherein the ALU is responsible for carrying out arithmetic and logical operations. This may include, addition, subtraction, multiplication, comparing two data, contrasting two data and the like. In one or more embodiments, processing unit may include a control unit wherein the control unit manages execution of instructions such that they are performed in the correct order. In none or more embodiments, processing unit may include registers wherein the registers may be used for temporary storage of data such as inputs fed into the processor and/or outputs executed by the processor. In one or more embodiments, processing unit may include cache memory wherein memory may be retrieved from cache memory for retrieval of data. In one or more embodiments, processing unit may include a clock register wherein the clock register is configured to synchronize the processor with other computing components. In one or more embodiments, processor 108 may include more than one processing unit having at least one or more arithmetic and logic units (ALUs) with hardware components that may perform arithmetic and logic operations. Processing units may further include registers to hold operands and results, as well as potentially "reservation station" queues of registers, registers to store interim results in multi-cycle operations, and an instruction unit/control circuit (including e.g. a finite state machine and/or multiplexor) that reads op codes from program instruction register banks and/or receives those op codes and enables registers/arithmetic and logic operators to read/output values. In one or more embodiments, processing unit may include a floating-point unit (FPU) wherein the FPU is configured to handle arithmetic operations with floating point numbers. In one or more embodiments, processor 108 may include a plurality of processing units wherein each processing unit may be configured for a particular task and/or function. In one or more embodiments, each core within multi-core processor may function independently. In one or more embodiments, each core within multi-core processor may perform functions in parallel with other cores. In one or more embodiments, multi-core processor may allow for a dedicated core for each program and/or software running on a computing system. In one or more embodiments, multiple cores may be used for a singular function and/or multiple functions. In one or more embodiments, multi-core processor may allow for a computing system to perform differing functions in parallel. In one or more embodiments, processor 108 may include a plurality of multi-core processors. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing devices operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory 112 between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a Processor module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, system 100 includes a memory 112 communicatively connected to processor 108, wherein the memory 112 contains instructions configuring processor 108 to perform any processing steps as described herein. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 112 may include a primary memory and a secondary memory. "Primary memory" also known as "random access memory" (RAM) for the purposes of this disclosure is a short-term storage device in which information is processed. In one or more embodiments, during use of computing device 104, instructions and/or information may be transmitted to primary memory wherein information may be processed. In one or more embodiments, information may only be populated within primary memory while a particular software is running. In one or more embodiments, information within primary memory is wiped and/or removed after computing device 104 has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 108 may access the information from primary memory.

Still referring to FIG. 1, System 100 may include a database 116. Database may include a remote database 116. Database 116 may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database 116 may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments. In one or more embodiments, computing device 104 may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by system computing device 104. In one or more embodiments, computing device 104 may transmit processes to server wherein computing device 104 may conserve power or energy.

With continued reference to FIG. 1, processor 108 is configured to receive an input matrix 120 having a plurality of electrocardiogram signals 124. A "Matrix" for the purposes of this disclosure is an array of numbers or characters arranged in rows or columns which are used to represent an object or properties of the object. For example, and without limitation, a matrix may be used to describe linear equations, differential equations, in a two-dimensional format. In another non limiting example, a matrix may be used to create graphs based on data points, generate statistical models and the like. "Input matrix" for the purposes of this disclosure is in array of numbers associated with an individual's health. For example, and without limitation, input matrix 120 may include an individual's recorded heart rates and times associated with the recorded heart rates. In one or more embodiments, input matrix 120 may include a plurality of electrocardiogram signals associated with a plurality of time variables 128. As used in the current disclosure, a "electrocardiogram signal" is a signal representative of electrical activity of heart. The ECG signal 124 may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves may provide information about the duration and regularity of various phases of the cardiac cycle. The ECG signal 124 may help diagnose various heart conditions, such as arrhythmias, myocardial infarction (heart attack), conduction abnormalities, and electrolyte imbalances. In one or more embodiments, ECG signals 124 may be received by one or more electrodes connected to the skin of an individual. In one or more embodiments, ECG signals 124 may represent depolarization and repolarization occurring in the heart. In one or more embodiments, ECG signals 124 may be captured periodically. For example, and without limitation, every second, every millisecond and the like. In one or more embodiments, each ECG signal 124 may contain an associated time variable 128. "Time variable 128" for the purposes of this disclosure is information indicating the time at which a particular ECG signal 124 was received. For example, and without limitation, time dependent variable may include, 5 ms, 10 ms, 15 ms and the like. In one or more embodiments, each ECG signal 124 may contain a time variable 128. In one or more embodiments, time variable 128 may increase in given increments, such as for example, in increments of 5 ms, wherein a first-time variable 128 may include 5 ms and a second time variable 128 may include 10 ms. In one or more embodiments, a combination of a plurality of ECG signals 124 and correlated time variable 128 may be used to generate a graph illustrating the heart functions of an individual. In one or more embodiments, input matrix 120 may include a plurality of ECG signals 124 and correlated time variable 128 during a given time frame such as, for example, over the span of a second, a minute, an hour, and the like. In one or more embodiments, ECG signals 124 may be captured as voltages, such as millivolts or microvolts.

With continued reference to FIG. 1, the plurality of electrocardiogram signals captures a temporal view of cardiac electrical activities. A "temporal view," as used in the current disclosure, refers to the analysis and visualization of heart-related events and phenomena over time. A temporal view may include patterns, changes, and dynamics of cardiac activity over time. A temporal view may include information surrounding the rhythm of the heart, including the regularity or irregularity of heartbeats. It allows for the identification of various rhythm abnormalities such as tachycardia (fast heart rate), bradycardia (slow heart rate), or arrhythmias (irregular heart rhythms). A temporal view of cardiac activities in three dimensions may refer to a visualization that represents the temporal evolution of cardiac events or phenomena in a three-dimensional space. It provides a comprehensive understanding of how various cardiac activities change over time. The ECG signal 124 may move through the 3D space of the heart over time. The signal does not just move forward in time, it also moves through the physical space of the heart, from SA node through atria, to AV node, and then through the ventricles. Such movement of the electrical signal through the heart's physical space over time can be referred to as "spatiotemporal excitation and propagation" which could be captured by plurality of ECG signals 124. It is essentially a way of observing and analyzing the timing and sequence of the heart's electrical activity as it moves through the physical structure of the heart. In the current case the dimensions may include axis representing time, spatial dimensions, and cardiac activity. By combining the temporal, spatial, and cardiac activity dimensions, the temporal view of cardiac activities in three dimensions allows for a comprehensive visualization and analysis of dynamic changes occurring within the heart. It can be used to study phenomena like electrical conduction, ventricular wall motion, valve function, blood flow dynamics, or the interaction between different regions of the heart. This visualization approach provides valuable insights into the complex temporal dynamics of cardiac activities and aids in understanding cardiac function, pathology, and treatment evaluation.

With continued reference to FIG. 1, input matrix 120 may be received through one or more input devices. "Input device" for the purposes of this disclosure is a device capable of transmitting information to computing device. For example, and without limitation, input device may include a keyboard, a mouse, a touchscreen, a smartphone, a network server, a sensor 132 and the like. In one or more embodiments, input device may include a sensor 132. In one or more embodiments, input matrix 120 and/or ECG signals 124 may be received by input device and/or sensor 132. As used in this disclosure, a "sensor" is a device that is configured to detect an input and/or a phenomenon and transmit information related to the detection. Sensor 132 may detect a plurality of data. A plurality of data detected by sensor 132 may include, but is not limited to, electrocardiogram signals, heart rate, blood pressure, electrical signals related to the heart, time variables 128 associated with captured data and the like. In one or more embodiments, and without limitation, sensor 132 may include a plurality of sensors 132. In one or more embodiments, and without limitation, sensor 132 may include one or more electrodes, and the like. Electrodes used for an electrocardiogram (ECG) are small sensors 132 or conductive patches that are placed on specific locations on the body to detect and record the electrical signals generated by the heart. Senor may serve as the interface between the body and the ECG machine, allowing for the measurement and recording of the heart's electrical activity. A plurality of sensors 132 may include 10 electrodes used for a standard 12-lead ECG, placed in specific positions on the chest and limbs of the patient. These electrodes are typically made of a conductive material, such as metal or carbon, and are connected to lead wires that transmit the electrical signals to the ECG machine for recording. In one or more embodiments, plurality of CG signals may be associated with a 12-lead electrocardiogram.

Proper electrode placement is crucial to ensure accurate signal detection and recording. In one or more embodiments, sensors 132 may include wireless sensors 132 wherein data may be received from sensor 132 to computing device wirelessly. In one or more embodiments, wireless sensors 132 may include Bluetooth enabled ECG sensors, RFID ECG sensors, Wi-Fi enabled ECG sensors and the like. In one or more embodiments, wireless sensors 132 may allow for receipt of data from a distance. In one or more embodiments, wireless sensors 132 may allow for a machine or system to receive data without wires connecting the sensors 132 to computing device. In one or more embodiments, the presence of wires from sensors 132 to computing device may obstruct medical personnel from conducting one or more medical treatment procedures.

With continued reference to FIG. 1, the plurality of sensors 132 may be placed on each limb, wherein there may be at least one sensor on each arm and leg. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line. In one or more embodiments, each sensor and/or lead may contain a set of electrical signals, wherein input matrix 120 may include ECG signals 124 associated with each lead and/or sensor.

With continued reference to FIG. 1, the plurality of sensors may include augmented unipolar sensors. These sensors may be labeled as aVR, aVL, and aVF. These sensors may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions. These leads capture the electrical signals from different orientations, which are then transformed into transformed coordinates to generate vectorcardiogram (VCG) representing magnitude and direction of electrical vectors during cardiac depolarization and repolarization. Transformed coordinates may include one or more a Cartesian coordinate system (x, y, z), polar coordinate system (r, θ), cylindrical coordinate system (p, q, z), or spherical coordinate system (r, θ, q). In some cases, transformed coordinates may include an angle, such as with polar coordinates, cylindrical coordinates, and spherical coordinates. In some cases, VCG may be normalized thus permitting full representation with only angles, i.e., angle traversals. In some cases, angle traversals may be advantageously processed with one or more processes, such as those described below and/or spectral analysis.

With continued reference to FIG. 1, in one or more embodiments, sensor 132 may include surface electrodes wherein the surface electrodes may be placed above the skin of a user and used to detect electrical impulses. In one or more embodiments, sensor 132 may further include a wearable ECG monitor wherein the wearable ECG monitor may be wrapped around a limb of the individual and used to detect electrical impulses. In one or more embodiments, sensor 132 may further include a Holter monitor, subdermal needle electrodes, and/or any other sensing device capable of receiving electrical signals.

With continued reference to FIG. 1, input matrix 120 may include a plurality of ECG signals 124 captured at discrete time intervals. In one or more embodiments, input matrix 120 may be generated and/or received in a digital imaging and communications in medicine (DICOM) Format, a CSV format, as a spread sheet containing cells for each datum and the like. In one or more embodiments, computing device may receive data in a raw format wherein the data may be converted into a matrix.

With continued reference to FIG. 1, sensors 132 and/or input devices are connected to a patient during an ablation procedure. In one or more embodiments, input matrix 120 may be received during an ablation procedure wherein input matrix 120 may contain information associated with an individual's heart during the procedure. "Patient" for the purposes of this disclosure is an individual who is receiving medical care. In one or more embodiments, patient may include an individual seeking medical attention, an individual seeking medical guidance, an individual receiving medical treatment and the like. In one or more embodiments, input matrix 120 may be received during an ablation procedure. "Ablation procedure" for the purposes of this disclosure is a process in which scars are made in the heart to block abnormal electrical signals. In one or more embodiments, a patient may contain an abnormal heart rhythm caused by irregular electrical signals wherein an ablation procedure may reduce or eliminate the abnormal electrical signals. In one or more embodiments, during an ablation procedure, heart tissue may be destroyed using radiofrequency, cryoablation, and the like. In one or more embodiments, during an ablation procedure, a cathode is guided through blood vessels to the heart and used to destroy heart tissue contributing to irregular heartbeats. In one or more embodiments, a medical professional may guide a catheter through a patient's blood vessels wherein the medical professional may identify, target, and eliminate heart tissue associated with the abnormal heart rhythms. In one or more embodiments, prior to an ablation procedure, a medical professional may map out and identify various portions of a patient's heart that may be contributing to irregular heart rhythms and electrical signals. In one or more embodiments, identified portions may be eliminated and/or damaged to prevent further irregular heart rhythms. In one or more embodiments, input matrix 120 may be received during an ablation procedure wherein input matrix 120 may contain information associated with a patient's electrical signals during the procedure. In one or more embodiments, input matrix 120 may be used to determine changes in electrical signals, changes in heart rhythm and the like. In one or more embodiments, input matrix 120 may be used to monitor an individual during the ablation procedure.

With continued reference to FIG. 1, processor 108 is configured to generate a cardiac vector 136 as a function of the input matrix 120. As used in the current disclosure, a "cardiac vector" is a transformed vector representative of an electrocardiogram. For example, and without limitation, a cardiac vector may include a three-dimensional vector containing information about magnitude and direction of electrical signals generated by heart during its depolarization and repolarization processes. A single cardiac vector 136 may be represented by the magnitude and direction of a plurality of ECG signals 124 generated from various sensor 132 located on the patient. The cardiac vector 136 may represent the net electrical forces generated by the heart at a specific point in time. The cardiac vector 136 may contain three components along three orthogonal axes: X, Y, and Z. The X-axis component may represent the anterior-posterior direction. The X-component indicates the movement of electrical vectors from the front (anterior) to the back (posterior) of the heart. The Y-axis component may represent the right-left direction. The y-axis component indicates the movement of electrical vectors from the right side to the left side of the heart. The Z-axis component may represent the superior-inferior direction. The Z-axis component indicates the movement of electrical vectors from the top (superior) to the bottom (inferior) of the heart. The magnitudes of these three components may determine the length of the cardiac vector 136, while their directions indicate the orientation of the vector in three-dimensional space. By analyzing the three-dimensional cardiac vector 136 over time, processor 108 can gain insights into the spatial orientation and sequence of the heart's electrical activity. This helps in diagnosing various cardiac conditions, assessing the spread of electrical impulses, and evaluating the overall electrical function of the heart. In one or more embodiments, cardiac vector 136 may provide spatial representation of the heart's electrical activity.

With continued reference to FIG. 1, processor 108 may generate a cardiac vector 136 by transforming ECG signals 124 and/or input matrix 120 into transformed coordinates using a transformation matrix. A "transformation matrix," for the purpose of this disclosure, is a mathematical tool used to perform transformations on objects in a coordinate system. It may include operations such as, without limitation, rotation, scaling, shearing, and translation (moving the whole object without changing its shape or orientation). In a non-limiting example, the transformation matrix may be used to map the information from a 12-lead ECG system into a 3-lead VCG system. Processor 108 may apply a linear transformation to plurality of ECG signals 124, wherein the application of the linear transformation may effectively change the basis of the coordinate system from a 12-lead ECG to a 3-lead VCG. In the field of vectorcardiography (VCG), the transformation matrix can play a role in mapping information from one system to another. For instance, a common example is mapping data from the 12-lead electrocardiogram (ECG) system to the 3-lead VCG system. In this scenario, the transformation matrix is applied to a set of ECG signals 124 in order to effectively change the basis of the coordinate system from the 12-lead ECG to the 3-lead VCG. In a non-limiting example, the ECG signals 124 may be represented by a matrix of dimensions 5000×12, with 5000 samples and 12 leads or sensors 132. The transformation matrix would have dimensions 12×3, representing the transformation from the 12-lead ECG system to the 3-lead VCG system. By multiplying the ECG matrix with the transformation matrix, the resulting matrix would have dimensions 5000×3, corresponding to the transformed VCG signals. The linear transformation performed by the matrix effectively changes the basis of the coordinate system, allowing the representation of the data in a different format or perspective. This transformation process facilitates the conversion of ECG information to the VCG system, enabling further analysis and interpretation based on the specific requirements and advantages of the VCG approach.

With continued reference to FIG. 1, a transformation matrix may include a selection of at least one lead system. As used in the current disclosure, a "lead system" is a configuration of electrodes placed on the body to measure and record electrical signals. A lead system may be used to capture the electrical activity of the heart or other physiological signals. The placement and arrangement of the electrodes in lead system determine the specific views or angles from which the electrical signals are recorded. In an embodiment, a lead system may be designed to provide a two-dimensional representation of the heart's electrical activity. It may consist of multiple leads placed on specific locations on the body to measure electrical potentials in different directions. A lead systems may use various arrangements of a plurality of sensors 132, which may include placing sensors 132 on limbs and the precordial area. Examples of lead systems may include a frank lead system, mason-likar lead system, XYZ lead system, dower lead system, first lead system, and the like. The sensors 132 placed on the limbs may be used to capture the electrical activity in the frontal plane, while sensors 132 in the precordial area provide information about the electrical activity in the horizontal plane. In another embodiment, a lead system may be specifically designed to capture and represent the three-dimensional nature of the heart's electrical activity. It involves using multiple electrodes positioned on the body to measure electrical vectors from different angles. Processor 108 may identify the location of each sensor 132 based on a manual input from a medical professional. Alternatively, processor 108 may identify the location of each sensor 132 based on the types.

With continued reference to FIG. 1, a lead system may include a first lead system. As used in the current disclosure, a "first lead system" is a group of sensors 132 that are positioned on the frontal plane (X-plane), the horizontal plane (Y-plane), and the coronal plane (Z-plane). These leads provide information about the heart's electrical activity from different perspectives and angles. The X-plane may refer to the imaginary plane that is perpendicular to the Y-plane of the body. In some embodiments, the X-plane may alternatively be labeled as the transvers plane. Sensors 132 located on the X-plane may be positioned along the midpoint between the two shoulders of the patient. Sensors 132 along the X-plane may capture the electrical activity in the anterior-posterior direction, representing the movement of electrical vectors from the front to the back of the body. The Y-plane is oriented in the right-left direction of the body. The Y-plane may be labeled as the sagittal plane or longitudinal plane. Sensors 132 along the Y-plane may detect movement of electrical vectors from the right side to the left side of the body. The sensors 132 position along the y-plane may be positioned on the midpoint between the jugular notch (suprasternal notch) and the umbilicus (at the xiphoid process) on the anterior midline of the body. By recording the electrical signals along the Y-plane, the sensors 132 provide information about the spatial orientation and movement of electrical vectors in the right-left direction.

With continued reference to FIG. 1, cardiac vector 136 may be calculated and/or generated through the use of a matrix equation such as:

$$V = TM * E$$

Wherein 'V' may denote the cardiac vector 136, 'TM' may denote the transformation matrix and 'E' denotes the ECG signals from the leads. In one or more embodiments, an expanded version of the matrix equation as illustrated above may be illustrated as:

$$\begin{bmatrix} V_X \\ V_y \\ V_Z \end{bmatrix} = (TM) * \begin{bmatrix} I \\ II \\ III \\ aVR \\ aVL \\ aVF \\ V1 \\ V2 \\ V3 \\ V4 \\ V5 \\ V6 \end{bmatrix}$$

With continued reference to FIG. 1, transformation matrix may include an Inverse dower transformation matrix. An inverse dower transformation matrix may create orthogonal leads and/or cardiac vector 136 through a transformation of 8 independent ECG leads as illustrated below:

| Lead | X | Y | Z |
| --- | --- | --- | --- |
| V1 | −0.172 | 0.057 | −0.229 |
| V2 | −0.074 | −0.019 | −0.310 |
| V3 | 0.122 | −0.106 | −0.246 |
| V4 | 0.231 | −0.022 | −0.063 |
| V5 | 0.239 | 0.041 | 0.055 |
| V6 | 0.194 | 0.048 | 0.108 |
| I | 0.156 | −0.227 | 0.022 |
| II | −0.010 | 0.887 | 0.102 |

With continued reference to FIG. 1, transformation matrix may include a Kors regression transformation matrix wherein transformation matrix may include a transformation of 8 independent leads such as:

| Lead | X | Y | Z |
| --- | --- | --- | --- |
| V1 | −0.130 | 0.06 | −0.430 |
| V2 | 0.05 | −0.020 | −0.060 |
| V3 | −0.010 | −0.050 | −0.140 |
| V4 | 0.14 | 0.06 | −0.200 |
| V5 | 0.06 | −0.170 | −0.110 |
| V6 | 0.54 | 0.13 | 0.31 |
| I | 0.38 | −0.070 | 0.11 |
| II | −0.070 | 0.93 | −0.230 |

With continued reference to FIG. 1, transformation matrix may further include linear regression-based transformations, Q least Square Value transformations (QLSV), a frank leads system and the like. In one or more embodiments, transformation matrix may convert an 8 lead ECG system into cardiac vector 136. In one or more embodiments, transformation matrix may convert a 12 lead ECG system to cardiac vector 136.

With continued reference to FIG. 1, the transformed coordinates into cardiac vector 136 may represent the magnitude and direction of the electrical vectors in three dimensions. The transformation process may vary based on the lead system and the transformation matrix that is being used. The ECG signals 124 are transformed to obtain transformed coordinates. The transformation equations may differ depending on the lead system and the transformation matrix being used. In a non-limiting example, in the first lead system, the standard Cartesian and/or polar transformation equations are used to derive the transformed coordinates from sensors 132 (I, II, and III) and sensors 132 (V1 to V6). These equations involve specific combinations of lead signals and coefficients. Using the transformed coordinates, the ECG signals 124 or each point in time are reconstructed in three-dimensional space. These cardiac vector 136 represent the direction and magnitude of the electrical activity at that specific moment during the cardiac cycle. In a non-limiting example, using the first lead system, the following processes to obtain the X, Y, and Z coordinates. When generating the X coordinates an ECG signal 124 from sensors 132 represented by I, II, III, aVR, aVL, aVF may be used. An example for the transformation equation within the transformation matrix for the X-axis may include: X=(0.3333*(aVR−aVL)). When generating the Y coordinates, an ECG signal 124 from sensors 132 112 represented by I, II, III, aVR, aVL, aVF may be used. An example for the transformation equation within the transformation matrix for the Y-axis may include: Y=(0.3333*(1+aVR+aVL)). When generating the Z coordinates, an ECG signal 124 from sensors 132 represented by I, II, III, aVR, aVL, aVF and V1 to V6 may be used. An example for the transformation equation within the transformation matrix may include: Z=(0.1667*(I+II+III+aVR+aVL+aVF+V3+V4−V5−V6)). These equations involve specific combinations of lead signals with different coefficients to calculate the X, Y, and Z coordinates. The coefficients are derived based on the principles of vectorcardiography and the orientation of the leads in the first lead system.

With continued reference to FIG. 1, processor 108 may generate a cardiac vector 136 by combining transformed coordinates from multiple sensors 132. The combination may involve adding the X, Y, and Z components of each ECG signal 124 to obtain the resultant X, Y, and Z components of the cardiac vector 136. The X, Y, and Z coordinates obtained from each ECG signal 124 are summed to calculate the overall X, Y, and Z components of the cardiac vector 136. This summation is performed by adding the corresponding values of X, Y, and Z from each sensor 132. This may include adding the X, Y, and Z coordinates from all the sensors 132 to obtain the resultant X, Y, and Z components of the cardiac vector 136. Using the resultant X, Y, and Z components obtained from the summation, the overall cardiac vector 136 is calculated. The cardiac vector 136 represents the net electrical forces generated by the heart at a specific point in time. The magnitude of the cardiac vector 136 1 may be determined by calculating the vector length using the Pythagorean theorem. For example, the magnitude may be calculated using a formula consisting of Magnitude=sqrt ($X^2+Y^2+Z^2$). The direction of the cardiac vector 136 may be determined by the orientation of the X, Y, and Z components in three-dimensional space. By combining the transformed coordinates obtained from multiple leads and calculating the overall cardiac vector 136, processor 108 and gain insights into the magnitude, direction, and orientation of the heart's electrical activity during its depolarization and repolarization processes.

With continued reference to FIG. 1, processor 108 may transform the plurality of electrocardiogram signals and/or input matrix 120 into a cardiac vector 136 using a vector machine-learning model. As used in the current disclosure, a "vector machine machine-learning model" is a machine-learning model that is configured to generate a cardiac vector 136. Vector machine machine-learning model may be consistent with the machine-learning model described below in FIG. 3. Inputs to the vector machine machine-learning model may include an ECG signal 124, lead system, transformation matrix, transformed components, examples of cardiac vectors 136, and the like. Outputs to the vector machine machine-learning model may include cardiac vectors 136 tailored to the electrocardiogram signals. Alternatively, outputs to the vector machine machine-learning model may include Cartesian and/or polar components associated with the cardiac vectors 136. Vector training data may include a plurality of data entries containing a plurality of inputs that are correlated to a plurality of outputs for training a processor 108 by a machine-learning process. In an embodiment, vector training data may include a plurality of electrocardiogram signals correlated to examples of cardiac vectors 136. Vector training data may be received from database 116. Vector training data may contain information about ECG signal 124, lead system, transformation matrix, Cartesian and/or polar components, examples of cardiac vector 136, and the like. In an embodiment, vector training data may be iteratively updated as a function of the input and output results of past vector machine machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model.

With continued reference to FIG. 1, transforming ECG signals 124 into cardiac vector 136 may include calculation of an electrical axis. "Electrical axis" for the purposes of this disclosure is a calculation indicating the direction of the electrical activity within the heart during depolarization. In one or more embodiments, electrical axis may be used to determine the QRS axis. In one or more embodiments, electrical axis may include a degree such as 30 degrees, 45 degrees, -30 degrees and the like wherein the particular degree may indicate the direction of the vector. In one or more embodiments, determining the electrical axis of the heart may aid in the diagnosis of various heart defects such as heart arrythmia. In one or more embodiments, a calculated degree of the electrical axis may allow for diagnoses of various heart irregularities. In one or more embodiments, a calculated electrical axis may fall under one of five electrical axis classifications; the normal axis, left axis deviation (LAD), right axis deviation (RAD), extreme axis deviation and indeterminate axis. In one or more embodiments, an electrical axis within the range of 0 to 90 degrees may fall within the normal axis classification, an electrical axis within the range of 90 to 180 may fall within RAD, an electrical axis within 0 to -90 may fall within LAD and an electrical axis within the range of -90 to 180 may fall within an extreme axis. In one or more embodiments, the electrical axis may be calculated using lead I and aVF wherein an inverse tangent of a sum of the ECG signals 124 of lead I divided by Lead aVF may be used to calculate the degree of the electrical axis (e.g. $Tan^{-1}$(Sum of Lead I/Sum of Lead aVF)).

With continued reference to FIG. 1, processor 108 may be configured to generate a vectorcardiogram image 140 as a function of the cardiac vector 136. As used in the current disclosure, a "vectorcardiogram image" is a representation of at least a cardiac vector 136, which may or may not be a graphical representation, but which may be visualized for display. The vectorcardiogram image 140 may be a graphical representation of the cardiac vector 136 over time. Placed in other words the vectorcardiogram image 140 includes a plot of the cardiac vector 136 lover a given time period, such as the cardiac cycle or a time period as denoted by time variables 128 within input matrix 120. The vectorcardiogram image 140 provides a visual depiction of the magnitude and direction of the electrical vectors generated by the heart during its depolarization and repolarization processes over time. A vectorcardiogram image 140 may include a Cartesian and/or polar axes. The vectorcardiogram image 140 is plotted in a three-dimensional coordinate system, where the X-axis represents the anterior-posterior direction, the Y-axis represents the right-left direction, and the Z-axis represents the superior-inferior direction. These axes provide a spatial reference for the magnitude and direction of the cardiac vectors 136. A vectorcardiogram image 140 may be described as a graphical representation of the cardiac vector 136, displaying the cardiac vector 136 over a period of time. In some cases, the time period may extend across several heart beats or a cardiac cycle. In some cases, the vectorcardiogram image 140 may include annotations of the P-wave, QRS complex, and T-wave, which are the characteristic waveforms of the electrical activity of the heart. These waveforms represent the depolarization and repolarization of the atria and ventricles. The placement and orientation of these waveforms within the vector loop 144 provides information about the spatial distribution and sequence of the electrical activity.

With continued reference to FIG. 1, the vectorcardiogram image 140 may include a vector loop 144. As used in the current disclosure, a "vector loop" is a graphical representation of the trajectory followed by the cardiac vector 136 during the cardiac cycle. It illustrates the changes in the magnitude and direction of the electrical vectors generated by the heart as it undergoes depolarization and repolarization. The vector loop 144 is a continuous curve that connects the Cartesian and/or polar coordinates obtained from different leads or electrodes throughout the cardiac cycle. It illustrates the changes in the magnitude and direction of the electrical vectors during each phase of the heart's electrical activity. The vector loop 144 is typically plotted in a two-dimensional plane, although it represents the three-dimensional nature of the cardio vector. The X and Y axes of the plot correspond to the anterior-posterior and right-left directions, respectively. The vector loop 144 is created by connecting the points that represent the X and Y coordinates of the cardiac vector 136 at each moment in time. The shape and characteristics of the vector loop 144 provide valuable information about the electrical activity of the heart. The vector loop 144 can take various shapes depending on the orientation and magnitude of the cardiac vector 136 during different phases of the cardiac cycle. The loop may be asymmetrical or irregular, reflecting abnormalities in the electrical conduction system or underlying cardiac conditions. The size of the vector loop 144 represents the magnitude or strength of the electrical vectors generated by the heart. A larger loop indicates a greater magnitude of electrical activity, while a smaller loop suggests a weaker or altered electrical conduction. The orientation of the vector loop 144 reflects the spatial direction of the electrical vectors. The loop may rotate or change its orientation during different phases of the cardiac cycle, providing information about the sequential activation and propagation of electrical impulses within the heart. Deviations of the vector loop 144 from the normal axis indicate abnormalities in the heart's electrical conduction system. Axis deviations can provide valuable diagnostic information, such as identifying the presence of left ventricular hypertrophy or bundle branch blocks.

With continued reference to FIG. 1, the vectorcardiogram image 140 may include a time-dependent depiction of the cardiac vector 136. A time-dependent depiction of a cardiac vector 136 refers to a graphical representation that shows the direction and magnitude of the electrical activity within the heart at a specific moment in time. This depiction is often visualized using a vector arrow or line, representing the vector of electrical forces generated by the heart. A time-dependent depiction of the cardiac vector 136 may provide valuable information about the electrical activation and conduction patterns of the heart. It helps clinicians assess the overall electrical axis and the spatial orientation of the heart's electrical activity. In an embodiment, a time-dependent cardiac vector 136 depiction may be displayed as a vector loop 144 or a sequence of vector arrows. The vector loop 144 is a closed curve that represents a complete cardiac cycle, showing the changes in the electrical vector throughout the cardiac cycle. It displays the direction and magnitude of the electrical forces generated by the heart in three-dimensional space. The starting point of the vector loop 144 is often referred to as the origin, and subsequent points along the loop may represent different time intervals during the cardiac cycle. The vector arrows connecting these points indicate the magnitude and direction of the electrical forces at those specific moments. The length and direction of the arrows convey information about the amplitude and orientation of the electrical vector. A time-dependent depiction of a cardiac vector 136 may include video of the cardiac vector 136. Additionally, when renditions of contiguous time slices are transformed into a video, the evolution of the spatial representation shape of each time slice over time not only reduces the cognitive overload of feature extraction by humans but also improves the ability to detect anomalies that are spread across both a single lead and multiple leads collectively over time.

With continued reference to FIG. 1, vectorcardiogram image 140 may include displaying the cardiac vector 136 through an alternative lag-reconstructed ECG representation. As used in the current disclosure, an "alternative lag-reconstructed ECG representation" is a method used to analyze and visualize the electrical activity of the heart by reconstructing the ECG signal 124 using time-delayed versions of itself. This approach is based on the concept that the dynamics of the cardiac electrical system can be captured by examining the relationship between different time points within the ECG waveform. Instead of representing the ECG signal 124 in the traditional format of voltage or amplitude over time, the lag-reconstructed representation may focus on creating a multidimensional space using delayed versions of the original ECG signal 124. Each dimension in this space corresponds to a time-delayed version of the ECG waveform. To create a lag-reconstructed ECG representation, a technique called time-delay embedding is typically employed. It involves selecting a suitable time delay parameter and embedding dimension. The time delay determines how far apart the time points in the reconstructed signal are, and the embedding dimension determines the number of delayed versions used for reconstruction. By reconstructing the ECG signal 124 in this manner, it becomes possible to capture and visualize the underlying dynamics and nonlinear properties of the cardiac electrical activity. This approach is particularly useful for analyzing and detecting patterns related to cardiac arrhythmias, heart rate variability, and other complex dynamics that may not be readily apparent in the traditional ECG representation. Once the lag-reconstructed ECG representation is obtained, various techniques such as phase space analysis, recurrence plots, or nonlinear dynamics methods can be applied to analyze and interpret the reconstructed signal. These methods can reveal information about the underlying dynamics, attractors, or recurrence patterns, which may provide insights into the cardiac system's behavior. Processor 108 may generate an alternative lag-reconstructed ECG representation by choosing appropriate time delay, which determines the separation between the time-delayed copies of the ECG signal 124. This time delay is often determined using techniques such as the mutual information or autocorrelation function. Processor 108 may generate lag vectors as a function of the time delay. Lag vectors may be created by taking successive samples of the ECG signal 124 at the chosen time delay. These lag vectors, also known as delay vectors, represent points in the reconstructed phase space. The embedding dimension refers to the number of components or variables used to construct each lag vector. It is often estimated using techniques such as the false nearest neighbors or correlation dimension. Once the lag vectors are constructed, they can be visualized in the reconstructed phase space. The resulting trajectory or attractor in the phase space can provide insights into the underlying dynamics of the ECG signal 124. Various nonlinear analysis techniques, such as fractal dimension estimation, recurrence quantification analysis, or Lyapunov exponent calculation, can be applied to analyze the reconstructed phase space and extract relevant information.

With continued reference to FIG. 1, processor 108 may generate vectorcardiogram image 140 using a transformation machine-learning model. As used in the current disclosure, a "transformation machine machine-learning model" is a machine-learning model that is configured to generate a vectorcardiogram image 140. Transformation machine machine-learning model may be consistent with the machine-learning model described below in FIG. 2. Inputs to the transformation machine machine-learning model may include an ECG signal 124, lead system, transformed coordinates, cardiac vector 136, examples of vectorcardiogram image 140, and the like. Outputs to the transformation machine machine-learning model may include vectorcardiogram image 140 tailored to the cardiac vector 136. Alternatively, outputs to the transformation machine machine-learning model may include a vector loop 144. Transformation training data may include a plurality of data entries containing a plurality of inputs that are correlated to a plurality of outputs for training a processor 108 by a machine-learning process. In an embodiment, transformation training data may include a plurality of cardiac vectors 136 correlated to examples of vectorcardiogram image 140. Transformation training data may be received from database 116. Transformation training data may contain information about ECG signal 124, lead system, transformed coordinates, cardiac vector 136, examples of vectorcardiogram image 140, and the like. In an embodiment, transformation training data may be iteratively updated as a function of the input and output results of past transformation machine machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model.

With continued reference to FIG. 1, vectorcardiogram image 140 may include one or more vector loops 144 wherein the vector loops 144 graphically represent the electrical activity of the heart. In one or more embodiments, variations in the vector loops 144 may indicate various abnormalities and/or disease associated with the patient. In one or more embodiments, vector loop 144 may include a QRS loop. A QRS loop may include a graphical representation of ventricular depolarization. In one or more embodiments, the QRS loop may indicate and/or illustrate the direction of electrical forces during ventricular depolarization. In one or more embodiments, the direction of electrical forces may be used to determine various disease states, various abnormalities associated with the heart of a user and the like. In one or more embodiments, various conditions such as myocardial infraction may be noticed through variations in the QRS loop wherein a particular variation may be attributed to myocardial infraction. In one or more embodiments, a vector loop 144 may depict the direction and magnitude of forces over a cardiac cycle. In one or more embodiments, vector loop 144 may further include a T loop wherein the T loop may indicate and/or illustrate the electrical forces during ventricular repolarization. In one or more embodiments, the T loop may focus on the repolarization phase while the QRS loop may focus on the depolarization phase. In one or more embodiments the combination of the QRS loop and the T loop may indicate changes in electrical forces over an entire cardiac cycle. In one or more embodiments, vector loop 144 may further include a P loop wherein the P loop illustrates and/or indicates electrical forces during atrial depolarization. In one or more embodiments, changes in P loop direction and/or magnitude may indicate various issues such as atrial arrhythmia. In one or more embodiments, the magnitude and direction of each vector loop 144 may indicate a particular issue associated with the patient. In one or more embodiments, vectorcardiogram image 140 may include one or more vector loops 144 wherein each vector loop 144 may be analyzed to determine a particular condition. In one or more embodiments, vectorcardiogram image 140 may be colored coded wherein each vector loop 144 may contain a differing color. In one or more embodiments, each vector loop 144 may contain a differing and distinct color wherein a medical professional may be able to easily discern between vector loops 144.

In one or more embodiments, vectorcardiogram image 140, vector loop 144 and/or cardiac vector 136 may be used to determine one or more ablative reactions 148. In one or more embodiments, processor 108 may be configured to determine at least one ablative reaction 148 as a function of vectorcardiogram image 140 In one or more embodiments, processor 108 may be configured to determine at least one ablative reaction 148 as a function of cardiac vector 136 and/or vector loop 144. "Ablative reaction," for the purposes of this disclosure, is information that can be used to facilitate an ablative procedure. For example, and without limitation, ablative reaction 148 may include information indicating that an individual contains an abnormal cardiac cycle and the source of the abnormality. In another non limiting example, ablative reaction 148 may include information indicating that a vector loop 144 may be abnormally shaped and thereby indicating a potential heart defect. In one or more embodiments, ablative reaction 148 may include changes in cardiac vectors 136 between cardiac cycles and/or between various portions of a cardiac cycles wherein changes in magnitude may indicate that a cardiac issue is present. In one or more embodiment, the cardiac health of an individual may be determined by changes in cardiac vectors 136, changes in vector loops 144 and/or using vectorcardiogram image 140. In one or more embodiments, an ablative reaction 148 may include any information that may assist a medical professional during medical treatment, medical guidance and/or a medical procedure. In one or more embodiments, ablative reaction 148 may include notifications of various heart abnormalities, such as arrythmia, myocardial infractions, conduction abnormalities, electrolyte imbalances and the like. In one or more embodiments, ablative reaction 148 may include information and/or steps to reduce and/or eliminate a particular abnormality. For example, and without limitation, ablative reaction 148 may include information indicating a particular heart tissue that requires scarring in order to eliminate the electrical signals causing the heart abnormalities. In one or more embodiments, ablative reaction 148 may be graphic wherein a user such as a medical professional may be able to visually see the exact issue. In one or more embodiments, ablative reaction 148 may be graphic wherein an image may be presented to the user depicting the particular issue. In one or more embodiments, ablative reaction 148 may be graphic wherein an image may illustrate a particular location in which heart abnormality has been found. In one or more embodiments, ablative reaction 148 may include a visual indicator that a heart abnormality has been found. Visual indication may include, but is not limited to, flashing lights, changes in color of various components within vectorcardiogram image 140, texts displayed on a display and the like. In one or more embodiments, ablative reaction 148 may include an audible alert 152. In one or more embodiments, system 100 may include an audio output device such as a speaker and/or any other sound emitting device that will notify a user that to focus their attention to a display communicatively connected to system 100. In one or more embodiments, system 100 may be communicatively connected to one or more remote devices, such as but not limited to, a smart phone, a desktop computer, a television screen, a smart watch, and the like wherein ablative reaction 148 may be transmitted to the remote device. In one or more embodiments, a user may be notified of a determination of ablative reaction 148 through remote device. In one or more embodiments, ablative reaction 148 may include information associated with one or more abnormal conduction pathways. "Conduction pathway" for the purposes of this disclosure is a route that electrical signals follow to stimulate contraction of the heart. Conduction pathways may include the sinoatrial (SA) node, wherein the SA node is located in the right atrium and configured to propagate electrical signals throughout the right atrium. The conduction of electrical impulses of the SA node are denoted as the P-wave. Electrical impulses from the Sa node may propagate through the right atrium and spread through the atria causing the heart to contract and pump blood. The electrical impulses from the SA node may travel through the Bachmann's bundle and to the left atrium. Conduction pathways may further include the atrioventricular (AV) node wherein the AV node is situated between the atria and the ventricles and is configured to provide a delay between the atria and the ventricles such that the ventricles are given sufficient time to fill with blood. In instances in which the atria and ventricles contract at the same time, blood would not be able to flow from the atria to the ventricles. Conduction pathways may further include pathways Bundle of His, wherein Bundle of His is a collection of heart muscles or fibers that transmit the electrical impulses to the left and right ventricles. Conduction pathways further include Purkinje fibers wherein Purkinje fibers stimulate the individual cells within the left and right ventricles. In one or more embodiments, ablative reaction 148 may contain information associated with one or more abnormal conduction pathways wherein a user such as a medical professional may be given notice as to which portions of the patient's heart requires attention. In one or more embodiments, ablative reaction 148 may include information associated with abnormal chambers wherein an abnormal chamber is a chamber of the heart that is not functioning properly.

With continued reference to FIG. 1, in one or more embodiments, ablative reaction 148 may be used to determine various heart abnormalities that need to be addressed during an ablative procedure. In one or more embodiments, ablative reaction 148 may be used to determine new heart abnormalities that occurred during the ablative procedure. For example, and without limitation, medical processional may scar heart tissue wherein the scarred heart tissue may result in electrical imbalances. In one or more embodiments, processor 108 may be configured to determine ablative reaction 148 only in instances in which a new heart abnormality is detected. In one or more embodiments, ablative reactions 148 determined at the beginning of the procedure may differ than ablative reactions 148 occurring during a procedure. For example, and without limitation, in instances in which processor 108 is configured to begin retrieving input matrix 120, various determined heart abnormalities may be determined and presented in a particular way. However, during a procedure, determined ablation procedure may differ wherein processor 108 may determine that a heart abnormality occurred during the procedure.

With continued reference to FIG. 1, in one or more embodiments, ablative reaction 148 may include information that a heart abnormality has been corrected. In one or more embodiments, a patient may be suffering from one or more heart abnormalities wherein the abnormalities may be corrected during an ablative procedure. In one or more embodiments, it may be beneficial to put a medical professional on notice that a particular abnormality has been corrected during the procedure. In one or more embodiments, ablative reactions 148 may differ based on the particular information analyzed. For example, an ablative reaction 148 associated with a detected abnormality may provide one set of information, audible alerts 152 and the like whereas an ablative reaction 148 associated with corrected abnormalities. In one or more embodiments, audible alerts 152 may differ wherein ablative reactions 148 associated with corrected issues may provide the medical professional with auditory notice that an issue was corrected whereas an ablative reaction 148 associated with detect issues may provide the medical professional with auditory notice that an issue has been detected.

With continued reference to FIG. 1, processor 108 may be configured to analyze cardiac vector 136, vector loops 144 and/or vectorcardiogram image 140 to determine ablative reaction 148. In one or more embodiments, processor 108 may be configured to determine abnormalities within vectorcardiogram image 140, cardiac vector 136, vector loop 144 and/or any other generated data as described in this disclosure to determine ablative reaction 148. In one or more embodiments, each ablative reaction 148 may differ based on the particular abnormality detected. For example, and without limitation, an ablative reaction 148 associated with a detected abnormal conduction pathways may differ from an ablative reaction 148 associated with a corrected issue. In one or more embodiments, ablative reactions 148 may differ based on the risk of harm to the patients wherein a small detected risk of harm may be associated with one ablative reaction 148 and a larger risk of harm may be associated with a differing ablative reaction 148.

With continued reference to FIG. 1, processor 108 may be configured to determine ablative reaction 148 by first assigning a diagnostic label 156 to the patient and then determining an ablative reaction 148 as a function of the diagnostic label 156. In one or more embodiments, processor 108 may be configured to assign a diagnostic label 156 as a function of the vectorcardiogram image 140 and/or cardiac vector 136. As used in the current disclosure, a "diagnostic label" is a label used describe a specific condition, disorder, or illness that affects an individual's health or heart structure or function. A diagnostic label 156 may be any specific condition, disorder, or illness, specifically associated with the heart. In a non-limiting example, diagnostic labels 156 may be associated with conditions related to the cardiac health such as normal sinus rhythm, atrial fibrillation, myocardial infarction, ventricular tachycardia, bundle branch bloc, arrythmias, ischemic heart disease, heart enlargement, conduction abnormalities, cardiac ischemia, electrolyte imbalances, and the like. Processor 108 may assign a diagnostic label 156 to a patient as function of the vectorcardiogram image 140 and/or cardiac vector.

Processor 108 may assign diagnostic label 156 by comparing the current vectorcardiogram image 140 to a plurality historical vectorcardiogram images 160. "Historical vectorcardiogram image" for the purposes of this disclosure is a vector cardiogram image generated on a previous day, previous iteration, by another patient, individual and the like. In one or more embodiments, historical vector cardiogram images may be retrieved from a database 116, a storage and the like. In one or more embodiments, plurality of historical cardiogram images may include vectorcardiogram images 140 and associated labels wherein each image may contain a particular diagnostic label 156. In one or more embodiments, a medical professional may aggregate a plurality of historical cardiogram images wherein each image may contain one or more diagnostic labels 156. In one or more embodiments, vector cardiogram images may be compared to a plurality of historical cardiogram images wherein a particular historical cardiogram image containing the same or similar cardiac vectors 136 may be used to assign a diagnostic label 156. In one or more embodiments, assigning a diagnostic label 156 may include comparing vector cardiogram image to a plurality of historical vector cardiogram images. The comparison may include comparing relevant features of the current vectorcardiogram image 140 to the historical vectorcardiogram images 160 for similarities or differences.

In one or more embodiments, processor 108 may be configured to perform image classification using an image classifier on a plurality of historical vector cardiogram images wherein processor 108 may be configured to detect various features of vector cardiogram image and assign diagnostic labels 156 based on the various features. An "image classifier," as used in this disclosure is a machine-learning model, such as a mathematical model, neural net, or program generated by a machine-learning algorithm known as a "classification algorithm," as described in further detail below, that sorts inputs of image information into categories or bins of data, outputting the categories or bins of data and/or labels associated therewith. Image classifier may be configured to output at least a datum that labels or otherwise identifies a set of images that are clustered together, found to be close under a distance metric as described below, or the like. Computing device and/or another device may generate image classifier using a classification algorithm, defined as a process whereby computing device derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In some cases, processor 108 may use an image classifier to identify a key image in data described in any data described in this disclosure. As used herein, a "key image" is an element of visual data used to identify and/or match elements to each other. An image classifier may be trained with binarized visual data that has already been classified to determine key images in any other data described in this disclosure. "Binarized visual data" for the purposes of this disclosure is visual data that is described in binary format. For example, binarized visual data of a photo may be comprised of ones and zeroes wherein the specific sequence of ones and zeros may be used to represent the photo. Binarized visual data may be used for image recognition wherein a specific sequence of ones and zeroes may indicate a product present in the image. An image classifier may be consistent with any classifier as discussed herein. An image classifier may receive input data (e.g. vectorcardiogram image 140) described in this disclosure and output a key image with the data. In an embodiment, image classifier may be used to compare visual data in data such as vectorcardiogram image 140 with visual data in another data set such as historical vector cardiogram images. Visual data in another data set may further include a plurality of visual data retrieved from database 116. In some cases, image classifier may identify one or more components within vectorcardiogram image 140. In some cases, image classifier may classify various vector loops 144, various cardiac vectors 136, and the like within cardiac image. In one or more embodiments, a particular vector loop 144, cardiac vector 136 and the like within cardiac image may be associated with a particular diagnostic label 156.

With continued reference to FIG. 1, processor 108 may employ pattern matching techniques to identify specific patterns or abnormalities within the vectorcardiogram image 140 to generate diagnostic label 156. This can involve comparing specific segments, intervals, or waveforms of the vectorcardiogram image 140 to detect similarities or differences. Cross-correlation, template matching, or dynamic time warping algorithms may be used for this purpose. Processor 108 may perform statistical analysis on various parameters derived from the vectorcardiogram image 140 to generate diagnostic label 156. This can involve calculating means, standard deviations, or other statistical measures for specific features or segments of the vectorcardiogram image 140. By comparing these statistical parameters, the computer can identify significant differences or similarities between the vectorcardiogram image 140 and a reference image and/or one or more historical vectorcardiogram images 160.

With continued reference to FIG. 1, processor 108 may utilize image classification. Edge detection one or more pattern matching techniques and the like to assign a diagnostic label 156. In one or more embodiments, each diagnostic label 156 may be associated with a particular pattern abnormality and the like within vectorcardiogram image 140. In one or more embodiments, processor 108 may receive a plurality of historical vectorcardiogram images 160 and determine at least one diagnostic label 156 as a function of the comparison. In one or more embodiments, each diagnostic label 156 may be associated with a particular ablative reaction 148 wherein determining the at least one diagnostic label 156 as a function of a comparison between the vectorcardiogram image 140 and the plurality of historical vectorcardiogram images 160 may include determining the at least one ablative reaction 148 as a function of a comparison between the vectorcardiogram image 140 and the plurality of historical vectorcardiogram images 160. In one or more embodiments, processor 108 may compare vectorcardiogram image 140 to plurality of historical vector cardiogram images using edge detection, image classification and/or any process as described in this disclosure. In one or more embodiments, a particular match between a vectorcardiogram image 140 and a historical vectorcardiogram image 160 may indicate a particular diagnostic label 156. In one or more embodiments, each historical vectorcardiogram image 160 may contain one or more diagnostic labels 156 wherein a degree of match between vectorcardiogram image 140 and historical vectorcardiogram image 160 may indicate a particular diagnostic label 156 for vectorcardiogram image 140.

With continued reference to FIG. 1, processor 108 may determine ablative reaction 148 using a using a lookup table and an assigned diagnostic label 156. A "lookup table," for the purposes of this disclosure, is an array of data that maps input values to output values. A lookup table may be used to replace a runtime computation with an array indexing operation. In another non limiting example, an educational action datum lookup table may be able to correlate educational obstacle datum to an educational action datum. Processor 108 may be configured to "lookup" one or more diagnostic labels 156 in order to find a corresponding ablative reaction 148. In one or more embodiments, a lookup table may contain a plurality of diagnostic labels 156 correlated to a plurality of ablative reactions 148 wherein a particular assigned diagnostic label 156 may indicate a particular ablative reaction 148. In one or more embodiments processor 108 may assign more than one diagnostic labels 156 wherein the more than one diagnoses labels may be looked up to determine the associated ablative reactions 148. In an embodiment, a diagnostic label 156 may include heart arrythmia wherein an associated ablative reaction 148 may include a procedure to treat heart arrhythmia. In one or more embodiments, ablative reaction 148 may contain diagnostic labels 156 wherein ablative reaction 148 may include the diagnosis as well as information associated with the diagnoses.

With continued reference to FIG. 1, processor 108 may be configured to determine various disease states and/or diagnostic labels 156 wherein processor 108 may be configured to determine ablative reaction 148. In one or more embodiments, changes in a cardiac vector 136 and/or vector loops 144 may indicate various diseases and/or abnormalities. In one or more embodiments, altered vector patterns may indicate issues associated with proper conduction through bundle branch blocks. In one or more embodiments, changes in the ST segment on cardiac vector 136 may indicate that a patient may be suffering a heart attack. In one or more embodiments, changes in the T wave may indicate cardiac hypertrophy. In one or more embodiments, irregular vector patterns may indicate arrythmia. In one or more embodiments, changes in T wave morphology, such as T wave inversion may indicate ischemia. In one or more embodiments, variations in vector loops 144, variations in morphology, variations in patterns and the like may be associated with various heart abnormalities. In one or more embodiments, the magnitude and direction of vector loops 144 may further indicate various abnormalities. In one or more embodiments, variations in magnitude and direction of cardiac vector 136 and/or vector loops 144 may indicate conduction abnormalities and/or hypertrophy. In one or more embodiments, a particular magnitude and/or change in magnitude may indicate a particular abnormality. In one or more embodiments, a particular vector shape, size and/or orientation may indicate particular abnormalities. In one or more embodiments, ST segment deviations, location of junction points, morphology in vector loops 144, changes in direction of electrical activity, and the like may indicate various heart abnormalities. In one or more embodiments, each change or set of changes within a cardiac vector 136 and/or vector loop 144 may be associated with a particular abnormality. For example, and without limitation, abnormalities between a relationship between P waves and QRS complexes may indicate issues within atrioventricular conduction. In one or more embodiments, processor 108 may be configured to compare cardiac vector 136, vector loop 144 and the like to a range of reference values wherein the range of reference values may indicate a range of acceptable values for each particular. In one or more embodiments, a range of reference values may include a range of values wherein data points, calculations, vectors and the like failing within the range of values may indicate that an individual does not contains a particular abnormality. In one or more embodiments, range of reference values may contain a plurality of reference values wherein each reference value may be associated with a different aspect of cardiac vector 136 and/or vector loop 144. For example, and without limitation, a first reference value may be used to determine proper T wave morphology, and a second reference value may be used to determine ST segmentation. In one or more embodiments, processor 108 may be configured to compare one or more portions and/or elements of vectorcardiogram image 140, cardiac vector 136 and/or vector loop 144 to determine one or more abnormalities. In one or more embodiments, processor 108 may be configured to determine ablative reaction 148 wherein processor 108 may compare vectorcardiogram image 140, cardiac loop and/or cardiac vector 136 to a plurality of reference values and/or a plurality of range of reference values. In one or more embodiments, processor 108 may determine which elements fall outside of one or more reference values. In one or more embodiments, processor 108 may determine ablative reaction 148 based on which elements fall outside of a particular range of reference values. For example, and without limitation, changes in the ST segment on cardiac vector 136 in comparison to a reference value may indicate that a patient may be suffering a heart attack. In one or more embodiments, failure to fall within a range of a particular reference value may indicate a particular ablative reaction 148. In one or more embodiments, a particular set of elements that fall outside of a particular set of reference values may indicate a particular diagnosis and/or ablative reaction 148. In one or more embodiments, processor 108 may utilize a lookup table wherein elements falling outside of a particular range may be correlated to a particular ablative reaction 148 and/or sets of ablative reactions 148 within the lookup table. In one or more embodiments, each reference value may be correlated to a particular heart abnormality and/or heart location. For example, and without limitation, in one or more embodiments, altered vector patterns may indicate issues associated with proper conduction through bundle branch blocks wherein a medical professional may be put on notice that the cause and/or location of the abnormality originates in the bundle branch blocks.

With continued reference to FIG. 1, in one or more embodiments, vectorcardiogram image 140, cardiac vector 136 and/or vector loop 144 may allow for visualization of electrical forces in different regions of the heart. In one or more embodiments, visualization of electrical forces may allow a medical professional to understand which portions of a patient's heart may require ablation. In one or more embodiments, vector cardiogram image, cardiac vector 136 and/or vector loop 144 may be used to determine which regions of a person's heart requires attention. In one or more embodiments, an element falling outside of a range of a particular reference value may indicate a particular region of the heart is behaving abnormally. In one or more embodiments, processor 108 may be configured to determine ablative reaction 148 by localizing an abnormality to at least one heart chamber. In one or more embodiments, a patient's heart may contain four chambers; the top 2 which are referred to as the right atrium and the left atrium, and the bottom two which are referred to as the right and left ventricles. In one or more embodiments, processor 108 may localize an abnormality to at least one heart chamber wherein processor 108 has determined a location and/or origin of the abnormality. In one or more embodiments, abnormalities may include elements falling outside of a range of reference values, diagnostic labels 156, defects in heart tissue and/or any other indication that a heart is not functioning properly. In one or more embodiments, processor 108 may localize an abnormality to at least one heart chamber wherein a medical professional may be put on notice as to the location of the abnormality that requires ablation. In a non-limiting example, may determine that a left ventricle of a patient's heart may be the origin of an issue in instances in which QRS vector may contain an abnormal shift to the left side of the ECG axis. In yet another non limiting example, processor 108 may determine that one of two atrial chambers are the origin of an abnormality due to irregularities with electrical activity in the area. In yet another non limiting example, processor 108 may determine that a right ventricle may the origin of a particular abnormality in instances in which cardiac vectors 136 and/or vector loops 144 associated with the right ventricle contain altered and/or inconsistent vector patterns. In yet another non limiting example, processor 108 may determine that a bundle branch block is the origin of the abnormality based on changes in vector orientation. In one or more embodiments, changes in vector orientation may further be used to determine which of the two sets of bundle branch blocks are the origin of the abnormality. In one or embodiments, processor 108 may determine an ablative reaction 148 as a function of the localized abnormality wherein ablative reaction 148 may contain information indicating the location of the abnormality, various steps to fix the abnormality, various steps to access the abnormality and the like. In one or more embodiments, the examples as provided above may be used to generate linear equations, look up tables associations between elements and ablative reactions 148 and the like. It is to be understood that the examples provided above are non-limiting and are merely presented for explanatory purposes.

With continued reference to FIG. 1, determining ablative reaction 148 may include generating a graphical visualization 150 of a chart. In one or more embodiments, the graphical visualization 150 may include an X-Y plot wherein time may be denoted along a horizontal axis (the X-axis) and distances may be denoted along a vertical axis (The Y-axis). In one or more embodiments, time may be graphed using time variables 128, wherein the time variables 128 received from sensor 132 may be used for graphing along a horizontal axis. In one or more embodiments, the vertical axis may be graphed using data points indicating deviations between cardiac cycles. In one or more embodiments, the Y axis may include cardiac deviations 154. A "Cardiac deviation" for the purposes of this disclosure is information indicating a change between cardiac data of successive time intervals. In some embodiments, cardiac deviation may include information indicating a change between data received at the onset of a QRS loop and data received at an offset of a QRS loop. For example, and without limitation, cardiac deviation 154 may contain a change in magnitude of a cardiac vector 136 and/or vector loop 144, changes in direction of electrical forces and the like. In one or more embodiments, during ablation procedures, cardiac vector 136 and/or vector loop 144 may be referred to as being 'opened' or 'closed'. For the purposes of this disclosure, a 'closed' cardiac vector 136 and/or vector loop 144 in a vector cardiogram indicates normal electrical activation signals and conduction signals in the heart. In a closed cardiac vector 136 and/or vector loop 144, a distinct P wave, RS complex and T wave may be present. In one or more embodiments, a closed cardiac vector 136 and/or vector loop may signify proper contraction which may indicate that an individual's heart is functioning properly. In one or more embodiments, a closed cardiac vector 136 and/or vector loop 144 may indicate a particular magnitude and direction of the vectors. In one or more embodiments, the magnitude and direction of cardiac vector 136 and/or vector loops may be consistent indicating organized and proper electrical activity. In one or more embodiments, a closed loop may contain synchronized directions wherein the synchronized directions indicate proper pumping and contractions of the heart. For the purposes of this disclosure an 'open' cardiac vector 136 and/or vector loop may indicate abnormalities in the heart's electrical conduction system. In one or more embodiments, an open cardiac vector 136 and/or vector loop may indicate that that the heart contains abnormal conduction such as irregular or disrupted electrical pathways. In one or more embodiments, an open loop may contain inconstant manufactured and directions wherein the inconsistency may indicate a particular disorder or heart arrythmia. In one or more embodiments, during ablation procedures, such as for example, Ventricular Tachycardia, the heart may produce signals corresponding to an open loop until the ablation procedures have concluded. If the ablation procedure had been successful, then the cardiac vector 136 and/or vector loop may change from an open cardiac vector 136 and/or vector loop to a closed cardiac vector 136 and/or vector loop 144. In one or more embodiments, cardiac deviation 154 may contain changes between loops wherein cardiac deviation 154 may include a positive number in instances in which a loop is opened and '0' or near-zero when the cardiac vector 136 and/or vector loop is closed. In one or more embodiments, graphical visualization 150 may include an X-Y-chart visualizing when cardiac vector 136 and/or vector loop is open or closed wherein a positive and/or nonzero number may indicate that the cardiac vector 136 and/or vector loop 144 is open and a zero may indicate that the cardiac vector 136 and/or vector loop 144 is closed. In one or more embodiments, computing device 104 may distinguish between an open loop and a closed loop by utilizing a distance metric. In some embodiments, cardiac deviation 154 may include a distance metric. In one or more embodiments, the distance metric may be used to determine a distance between two vectors at different given points. Distance metric may include the difference between a first vector at the onset of a QRS loop of a vectorcardiogram and a second vector at the offset of the QRS loop of the vectorcardiogram. For example, computing device 104 may be configured to measure cardiac vector 136 and/or vector loops 144 between two given heartbeats, wherein a particular difference in magnitude and direction for the two cardiac vector 136 and/or vector loops 144 may indicate if the cardiac vector 136 and/or vector loop 144 is open or closed. In one or more embodiments, distance metric may further include the Euclidean Distance between two cardiac vectors 136 at successive time intervals. Each cardiac vector 136 may include a 3-d spatial vector and the Euclidean distance between them may be small if the vector has not changed its magnitude and direction. In instances, in which vector loop 144 and/or cardiac vector is closed, the Euclidean distance between cardiac vectors may be small and/or unchanged. In one or more embodiments, successive time intervals may include but are not limited to, the time between the start of a cardiac cycle and the end of a cardiac cycle, the duration of the QRS complex, the time between the start of the Q wave and the end of the T wave, the time between successive R waves and the like. In one or more embodiments, distance metric may include a "distance squared" comparison wherein the distance between cardiac vectors 136 may be squared to increase optimization. In one or more embodiments, Euclidian distance may include the measure of a straight-line distance between two points in Euclidian space. In one or more embodiments, in a three-dimensional space, the Euclidian distance may be measured using the Pythagorean theorem. In one or more embodiments, the cardiac deviation includes a Euclidean distance between two cardiac vectors 136 at successive time intervals. In one or more embodiments, changes recorded as a result of the distance metric may be used as cardiac deviations 154. In one or more embodiments, consecutive cardiac vector 136 and/or vector loops 144 (e.g. two cardiac vector 136 and/or vector loops received from consecutive heart beats) may be compared to one another wherein smaller cardiac deviations 154 or changes in distances may indicate that the cardiac vector 136 and/or vector loops 144 are closed, and larger cardiac deviations 154 or distances may indicate that the cardiac vector 136 and/or vector loops 144 are open. In one or more embodiments, determining an ablative reaction 148 may include determining if cardiac vector 136 and/or vector loop 144 is open or closed. In one or more embodiments, in instances in which the distance between two cardiac vector 136 and/or vector loops increases and/or cardiac deviation 154 increases, computing device 104 may determine that cardiac vector 136 and/or vector loop 144 is open and a particular heart issue is present. In one or more embodiments, distances between cardiac vector 136 and/or vector loops 144 may include distances between points on a vectorcardiogram loop at the onset of the QRS loop and the offset of the QRS loop. In one or more embodiments, the distance between the onset of the QRS loop and the QRS loop may represent the duration of ventricular depolarization. In one or more embodiments, distances and/or cardiac deviations 154 may be measured in time such as milliseconds. In one or more embodiments, abnormalities in duration may indicate various cardiac conditions. In one or more embodiments, the morphology of a QRS loop may be determined, wherein the morphology refers to the shape or form of the QRS complex and/or QRS loop. In one or more embodiments, changes in QRS morphology may indicate various cardiac conditions. In one or more embodiments, changes within QRS morphology may be recorded as cardiac deviations 154 wherein cardiac deviation 154 may contain the rate of change, the change at a particular moment and the like. In one or more embodiments, ST-segment elevation, Q waves and t-wave abnormalities may all be a part of the QRS morphology. In one or more embodiments, changes in a QRS loop such as duration amplitude and shape between an onset of the QRS loop and an Offset of the QRS loop may be used to determine various cardiac abnormalities wherein changes may be recorded as cardiac deviations 154. In one or more embodiments, in instances in which the distance between two cardiac vector 136 and/or vector loops stay the same or decrease, computing device 104 may determine that the cardiac vector 136 and/or vector loop 144 is closed. In one or more embodiments, computing device may determine if cardiac vector 136 and/or vector loop is open or closed by comparing cardiac vector 136 and/or vector loop to one or more thresholds, wherein a magnitude and direction outside of the threshold may indicate that a cardiac vector 136 and/or vector loop is open. In one or more embodiments, computing device may compare cardiac vector 136 and/or vector loops from each heartbeat wherein a particular change in magnitude or direction between two cardiac vector 136 and/or vector loops 144 may indicate whether a cardiac vector 136 and/or vector loop 144 is open or closed. In one or more embodiments, in instances in which differences or distances between cardiac vector 136 and/or vector loops 144 are asymptotically low, computing device 104 may determine that the cardiac vector 136 and/or vector loop is closed. In one or more embodiments, ablative reaction 148 may include information indicating whether cardiac vector 136 and/or vector loop 144 is open or closed. In one or more embodiments, ablative reaction may change during a procedure wherein cardiac vector 136 and/or vector loop 144 may be open initially and closed following success of the procedure. In one or more embodiments, a medical professional may be put on notice that the procedure was successful through the determination of open or closed cardiac vector 136 and/or vector loops 144. In one or more embodiments, following the success of an ablation procedure the distance between two given cardiac vector 136 and/or vector loops and/or cardiac deviation 154 may start to decrease and/or may not increase such that computing device 104 may determine that the cardiac vector 136 and/or vector loop has been closed. In one or more embodiments, following a successful ablation procedure, the distance between two cardiac vector 136 and/or vector loops and/or cardiac deviation 154 may not decrease immediately and instead may stay stagnant for a short period. In one or more embodiments, a stagnant change may further indicate that cardiac vector 136 and/or vector loop has been closed.

With continued reference to FIG. 1, ablative reaction may include at least an X-Y plot wherein cardiac deviations 154 are plotted over a given time. In one or more embodiments, in instances in which cardiac deviation 154 may be increasing over time on the X-Y plot, a medical professional may be put on notice that a particular abnormality is present. In one or more embodiments, in instances in which cardiac deviation 154 is decreasing over time and/or does not continue to increase, a medical professional may be put on notice that the abnormality has been corrected. In one or more embodiments, during ablation procedures, an abnormality may be targeted and corrected wherein X-Y plot may allow a medical professional to visually see changes in cardiac activity as a function of time. In one more embodiment, graphical representation may include a two dimensional graphical representation wherein time may be denoted along an X-axis and/or horizontal axis and cardiac deviations 154 may be denoted along the Y-axis and/or vertical axis. In one or more embodiments, cardiac deviation 154 may contain changes in duration and/or amplitude of QRS loops. In one or more embodiments, duration may include the time it takes for electrical impulses to travel through the ventricles wherein changes in duration may be recorded as cardiac deviations 154. In one or more embodiments, amplitude may refer to the height of the QRS loops wherein the height may be representative of the strength of the electrical signal. In one or more embodiments, changes in amplitude may be recorded as cardiac deviations 154. In one or more embodiments, deviations within cardiac deviation 154 may be recorded at similar points during a cardiac cycle. For example, and without limitation, a first data point may be received during a first instance during a first cardiac cycle and a second data points may be received during a first instance during a second cardiac cycle wherein changes between the first point and the second point may be recorded as cardiac deviations 154. In one or more embodiments, cardiac deviation 154 may indicate changes between two cardiac cycles such as changes in amplitude, changes in duration and the like. In one or more embodiments, cardiac deviation may include a change in cardiac cycles. In one or more embodiments, cardiac deviation includes a change in magnitude between the cardiac vector 136 at the start of a cardiac cycle and the cardiac vector 136 at the end of a cardiac cycle. In one or more embodiments, graphical representation of X-Y ploy may allow for a medical professional to quickly determine changes in QRS loops. In one or more embodiments, a patient's heart may beat around 80 times per minute wherein manual determinations by a medical professional between each beat can take hours to manually determine. In one or more embodiments, a medical professional may quickly view the graphical visualization 150 of the X-Y plot to easily determine changes in deviations and overall trends. In one or more embodiments, ablative reaction may include at least graphical visualization 150 wherein graphical visualization 150 includes an X-Y plot of cardiac deviations along a vertical axis and time variables along the horizontal axis. This may be described in further detail such as in reference to FIG. 2

With continued reference to FIG. 1, in one or more embodiments, ablative reactions 148 may be used to modify vectorcardiogram image 140. In one or more embodiments, determining at least one ablative reaction 148 for the vectorcardiogram image 140 includes assigning an ablative color 164 to each of the one on one or more vector loops 144. "Ablative color" for the purposes of this disclosure is a set of colors that convey information associated with an ablative procedure. For example, and without limitation, an ablative color 164 of red may indicate an issue during the ablative procedure, while an ablative color 164 of green may indicate no issues and/or a corrected during the ablative procedure. In one or more embodiments, each color may convey a particular set of information, such as but not limited to, attention needed, an issue has occurred, an issue has been resolved, an abnormality is occurring in a particular location, a particular location requires attention, an ablative procedure is occurring in a particular region of the heart and the like. In one or more embodiments, ablative colors 164 may be used to convey information to medical personnel who can quickly understand an issue based on a color present. In one or more embodiments, the presence of colors may convey information to medical personnel during an ablative procedure without a requirement to read text and/or characters. In one or more embodiments, vectorcardiogram image 140 may be modified wherein cardiac vector 136, vector loops 144 and/or portions thereof may contain ablative colors 164. In one or more embodiments, processor 108 may determine a cardiac vector 136, vector loop 144 and/or portions thereof within cardiac image that convey an abnormality and assign an ablative color 164 to the cardiograph image. In one or more embodiments, processor 108 may be configured to assign an ablative color 164, such as red, to vector loops 144 that are behaving abnormally. In one or more embodiments, medical personnel may view vectorcardiogram image 140 and determine that a particular section of the heart and/or a particular abnormality is occurring based on a colored vector loop 144. In one or more embodiments, vector loops 144 may be assigned colors based on determinations made by processor 108. In one or more embodiments, ablative colors 164 may be used to visually display abnormalities on cartographic image. In one or more embodiments, ablative colors 164 may indicate the severity of an abnormality wherein, for example, abnormality that can contribute to serious health issues may be colored a dark red whereas abnormalities that can contribute to lesser serious health issues may be colored a lighter red. In one or more embodiments, during an ablative procedure, a medical professional may target one or more area of the heart that requires ablation. In one or more embodiments, following each ablation, ablative colors 164 associated with vector loops 144 may change shades, colors and the like to indicate that an abnormality has been treated, has gotten less severe and the like. In one or more embodiments, ablative colors 164 may be used to indicate that an issue may still be present and/or that the issue has been fully resolved. For example, and without limitation, a vector loop 144 may turn to a lighter shade of a particular to indicate that while an ablation did somewhat treat an abnormality, there are still other issues remaining. In one or more embodiments, medical professionals may make misguided determinations about what area requires ablation. In one or more embodiments, ablative colors 164 may be used to indicate that an area has been treated and therefore no further ablation is required. In one or more embodiments, ablative colors 164 may indicate that a new issue and/or abnormality has arisen as a result of the ablation. In one or more embodiments, a medical professional may visually see in real time the status of an individual's heart wherein the medical professional may determine if and/or when a procedure has concluded. In one or more embodiments, processor 108 may assign ablative colors 164 to particular vector loops 144 based on detected abnormalities. In one or more embodiments, input matrix 120 may be continuously received wherein ablative colors 164 may differ throughout a particular time frame. For example, and without limitation, a vector loop 144 may be initially green wherein receipt of additional electrocardiogram signals may cause a vector loop 144 to change colors. In one or more embodiments, ablative reaction 148 may be responsive to the actions of a medical professional, wherein ablations and/or other treatments done to the patient may be reflected within electrocardiogram signals received during the treatment.

With continued reference to FIG. 1, processor 108 may be configured to determine at least one ablative reaction 148 as a function of a machine learning model. The machine learning model may include any machine learning model as described in this disclosure. Processor 108 may use a machine learning module, such as a cardiographic machine learning module for the purposes of this disclosure, to implement one or more algorithms or generate one or more machine-learning models, such as a cardiographic machine learning model 168 to create and/or determine one or more ablative reactions 148. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from database 116, such as any database 116 described in this disclosure, or be provided by a user. In other embodiments, a machine-learning module may obtain a training set by querying a communicatively connected database 116 that includes past inputs and outputs. Training data may include inputs from various types of databases 116, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to categories by tags, tokens, or other data elements. A machine learning module, such as cardiographic machine learning module, may be used to create cardiographic machine learning model 168 and/or any other machine learning model using training data. Cardiographic machine learning model 168 may be trained by correlated inputs and outputs of training data. Training data may be data sets that have already been converted from raw data whether manually, by machine, or any other method. Cardiographic training data 172 may be stored in database 116. Cardiographic training data 172 may also be retrieved from database 116. In some cases cardiographic machine learning model 168 may be trained iteratively using previous inputs correlated to previous outputs. For example, processor 108 may be configured to store vectorcardiogram images 140, and/or any other data as described in this disclosure from current iteration and one or more ablative reactions 148 to train the machine learning model. In some cases, the machine learning model may be trained based on user input 176. For example, a user may indicate that one or more ablative reactions 148 are inaccurate wherein the machine learning model may be trained as a function of the user input 176. In some cases, the machine learning model may allow for improvements to computing device such as but not limited to improvements relating to comparing data items, the ability to sort efficiently, an increase in accuracy of analytical methods and the like.

With continued reference to FIG. 1, cardiographic machine learning model 168 may receive vectorcardiogram image 140 and/or cardiac vectors 136 as an input and determine one or more ablative reactions 148. In one or more embodiments, vectorcardiogram image 140 may include a plurality of vectorcardiogram images 140 wherein each vectorcardiogram image 140 denotes a differing time frame. In one or more embodiments, data such as input matrix 120 may be continuously retrieved throughout an iteration wherein vectorcardiogram image 140 may change upon receipt of additional data. In one or more embodiments, processor 108 may be configured to capture cardiographic at a particular point in time to determine ablative reaction 148. In one or more embodiments, cardiographic machine learning model 168 may receive vectorcardiogram image 140 and output one or more ablative reactions 148. In one or more embodiments, cardiographic machine learning model 168 may be trained with cardiographic training data 172. In one or more embodiments, cardiographic training data 172 may contain a plurality of vectorcardiogram images 140 correlated to a plurality of ablative reactions 148. In one or more embodiments, cardiographic training data may contain a plurality of vector loops 144 and/or cardiac vector correlated to a plurality of ablative reactions 148 wherein a particular cardiac vector 136 and/or vector loop 144 may be associated with a particular ablative reaction 148. In an embodiment, a particular vectorcardiogram image 140 may be correlated to one or more ablative reactions 148. In one or more embodiments, cardiographic training data 172 may be generated by a user, third party and the like. In one or more embodiments, cardiographic training data 172 may be received from a database 116, cloud server, network server and the like. In one or more embodiments, cardiographic training data 172 may contain vectorcardiogram images 140 from previous iteration and correlated ablative reactions 148. In one or more embodiments cardiographic machine learning model 168 may be training as a function of cardiographic training data 172. In one or more embodiments, ablative reaction 148 may be determined as a function of vectorcardiogram image 140 and/or cardiographic machine learning model 168.

With continued reference to FIG. 1, cardiographic machine learning model 168 may be iteratively trained. In one or more embodiments, cardiographic machine learning model 168 may receive a plurality of vectorcardiogram images 140 over a particular timeframe associated with a patient and determine one or more ablative reactions 148. In one or more embodiments, two or more vectorcardiogram images 140 may contain similar data but captured at different time intervals. In one or more embodiments, cardiographic machine learning model 168 may output ablative reactions 148 for each vectorcardiogram image 140 received. In one or more embodiments, cardiographic machine learning model 168 may be iteratively trained wherein cardiographic machine learning model 168 may receive a set of similar vectorcardiogram images 140 and compare the determined ablative reactions 148. In one or more embodiments, a comparison of similar input data may indicate if one or more outputs are correct. For example, and without limitation, in an instance in which an ablative reaction 148 is present in a first vectorcardiogram image 140 and a second vectorcardiogram image 140, it may be possible that cardiographic machine learning model 168 missed an ablative reaction 148 and/or the abnormality causing the ablative reaction 148 has be resolved. However in instances in which a third vectorcardiogram image 140 contains the same ablative reaction 148, it may not be possible that a first vectorcardiogram image 140 output a particular ablative reaction 148, the second vectorcardiogram image 140 didn't and the third vectorcardiogram image 140 again indicated the same ablative reaction 148. In one or more embodiments, cardiographic machine learning model 168 may be iteratively trained by comparing sets of similar vectorcardiogram images 140 to their correlated outputs. In one or more embodiments, it may be possible that an ablative reaction 148 was incorrectly determined based on a comparison of a set of vectorcardiogram images 140. In one or more embodiments, cardiographic machine learning model 168 may be iteratively trained by comparing sets of vectorcardiogram images 140 and their associated ablative reactions 148. In one or more embodiments, comparing sets of vectorcardiogram images 140 may indicate that a particular ablative reaction 148 in one of the vectorcardiogram images 140 was incorrectly determined. In one or more embodiments, cardiographic machine learning model 168 may be iteratively trained wherein vectorcardiogram images 140 and correlated outputs of the machine learning model may be used for future iterations. In one or more embodiments, cardiographic machine learning model 168 may be iteratively trained wherein processor 108 cardiographic machine learning model 168 may use vectorcardiogram images 140 from a current iteration for future iterations. In one or more embodiments, cardiographic machine learning model 168 may be iteratively trained wherein in instances in which an input is unrecognized, cardiographic machine learning model 168 may use previously received inputs and subsequent inputs to 'recognize' the input for future iterations. For example, and without limitation, a first vectorcardiogram image 140 may indicate heart arrythmia, a second vectorcardiogram image 140 may come out as 'unrecognized', and a third vectorcardiogram image 140 may indicate heart arrythmia again. In such an instance cardiographic machine learning model 168 may be trained such that the second vectorcardiogram image 140 may indicate heart arrythmia as well based on a consistent pattern.

With continued reference to FIG. 1, cardiographic machine learning model 168 may be iteratively trained as function of user input 176. "User input" for the purposes of this disclosure is an input made by an individual interacting with system 100. In one or more embodiments, user input 176 may include the clicking of a button, the insertion of characters through an input device, interaction with a user interface and the like. In one or more embodiments, cardiographic machine learning model 168 may be iteratively trained wherein a medical professional may indicate if a particular ablative reaction 148 as an output is correct. In one or more embodiments, a medical professional may indicate that one or more diagnoses and/or ablative reactions 148 for a vectorcardiogram image 140 are incorrect, wherein the medical professional may input the correct ablative reactions 148. In one or more embodiments, cardiographic machine learning model 168 may be iteratively trained for subsequent iterations.

With continued reference to FIG. 1, ablative reactions 148 may include colors, notifications information and/or any other information that may convey a message to a medical professional performing an ablative procedure. In one or more embodiments, ablative reaction 148 may include a diagram of the heart of an individual with an indication as to the location of an abnormality. For example, and without limitation, ablative reaction 148 may include an image or a sketch of heart and a location as to the origin of a particular issue. In one or more embodiments, a user interface may contain an image of a heart, wherein ablative reaction 148 may include visualizations on the image indicating the source of the abnormality. This may be explained in further detail below.

With continued reference to FIG. 1, processor 108 may be configured to create a user interface data structure. As used in this disclosure, "user interface data structure" is a data structure representing a specialized formatting of data on a computer configured such that the information can be effectively presented for a user interface. User interface data structure may include cardiac vector 136, vectorcardiogram image 140, ablative reaction 148 and the like.

With continued reference to FIG. 1, processor 108 may be configured to transmit the user interface data structure to a graphical user interface. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Processor 108 may transmit the data described above to database 116 wherein the data may be accessed from database 116. Processor 108 may further transmit the data above to a device display or another computing device.

With continued reference to FIG. 1, system may include a graphical user interface (GUI). For the purposes of this disclosure, a "user interface" is a means by which a user and a computer system interact. For example, through the use of input devices and software. In some cases, processor 108 may be configured to modify graphical user interface as a function of the ablative reactions 148 and/or vectorcardiogram images 140 by populating user interface data structure and visually presenting the data through modification of the graphical user interface. A user interface may include graphical user interface, command line interface (CLI), menu-driven user interface, touch user interface, voice user interface (VUI), form-based user interface, any combination thereof and the like. In some embodiments, a user may interact with the user interface using a computing device distinct from and communicatively connected to processor 108. For example, a smart phone, smart tablet, or laptop operated by the user and/or participant. A user interface may include one or more graphical locator and/or cursor facilities allowing a user to interact with graphical models and/or combinations thereof, for instance using a touchscreen, touchpad, mouse, keyboard, and/or other manual data entry device. A "graphical user interface," as used herein, is a user interface that allows users to interact with electronic devices through visual representations. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in graphical user interface. Persons skilled in the art, upon reviewing the entirety of this disclosure, will be aware of various ways in which a graphical user interface and/or elements thereof may be implemented and/or used as described in this disclosure. In one or more embodiments, graphical user interface may include a graphical visualization of the human heart and various locations as to which attention may be needed. In one or more embodiments, ablative reaction 148 may be used to pinpoint the components of the heart that are acting abnormally and indicate the exact issue.

With continued reference to FIG. 1, system 100 may further include a display device communicatively connected to at least a processor 108. "Display device" for the purposes of this disclosure is a device configured to show visual information. In some cases, display device may include a liquid crystal display (LCD), a cathode ray tube (CRT), a plasma display, a light emitting diode (LED) display, and any combinations thereof. Display device may include, but is not limited to, a smartphone, tablet, laptop, monitor, tablet, and the like. Display device may include a separate device that includes a transparent screen configured to display computer generated images and/or information. In some cases, display device may be configured to visually present one or more data through GUI to a user, wherein a user may interact with the data through GUI. In some cases, a user may view GUI through display.

With continued reference to FIG. 1, system 100 may include and/or be included within a mobile unit. "Mobile unit" for the purposes of this disclosure is a device that is capable of being transported from one location to another. In one or more embodiments, mobile unit may include wheels that allow mobile unit to be moved from one location to another. In one or more embodiments, display device may be located atop mobile unit wherein a user may navigate mobile unit with display device around a room. In one or more embodiments, mobile unit may contain a battery pack wherein computing device may be powered by battery back. In one or more embodiments, battery pack may be rechargeable. In one or more embodiments, one or more processes as described above, such as but not limited to processing relating to machine learning models, may be computed on a cloud, network server and the like to save on battery power. In one or more embodiments, mobile unit may allow for system 100 to be navigated throughout an operating room. In one or more embodiments, location of mobile unit may differ for each patient and/or procedure. In one or more embodiments, sensors 132 as described above may be connected to mobile unit wherein mobile unit may be navigated closer to and/or further away from patient based on the location of sensors 132. In one or more embodiments, sensors 132 may contain wiring that needs to be physically connected to mobile unit. In one or more embodiments, mobile unit may allow for movement of system 100 from one location to another in instances in which movement may be needed. Mobile unit may be described in further detail below such as in reference to FIG. 2

Figure 2:
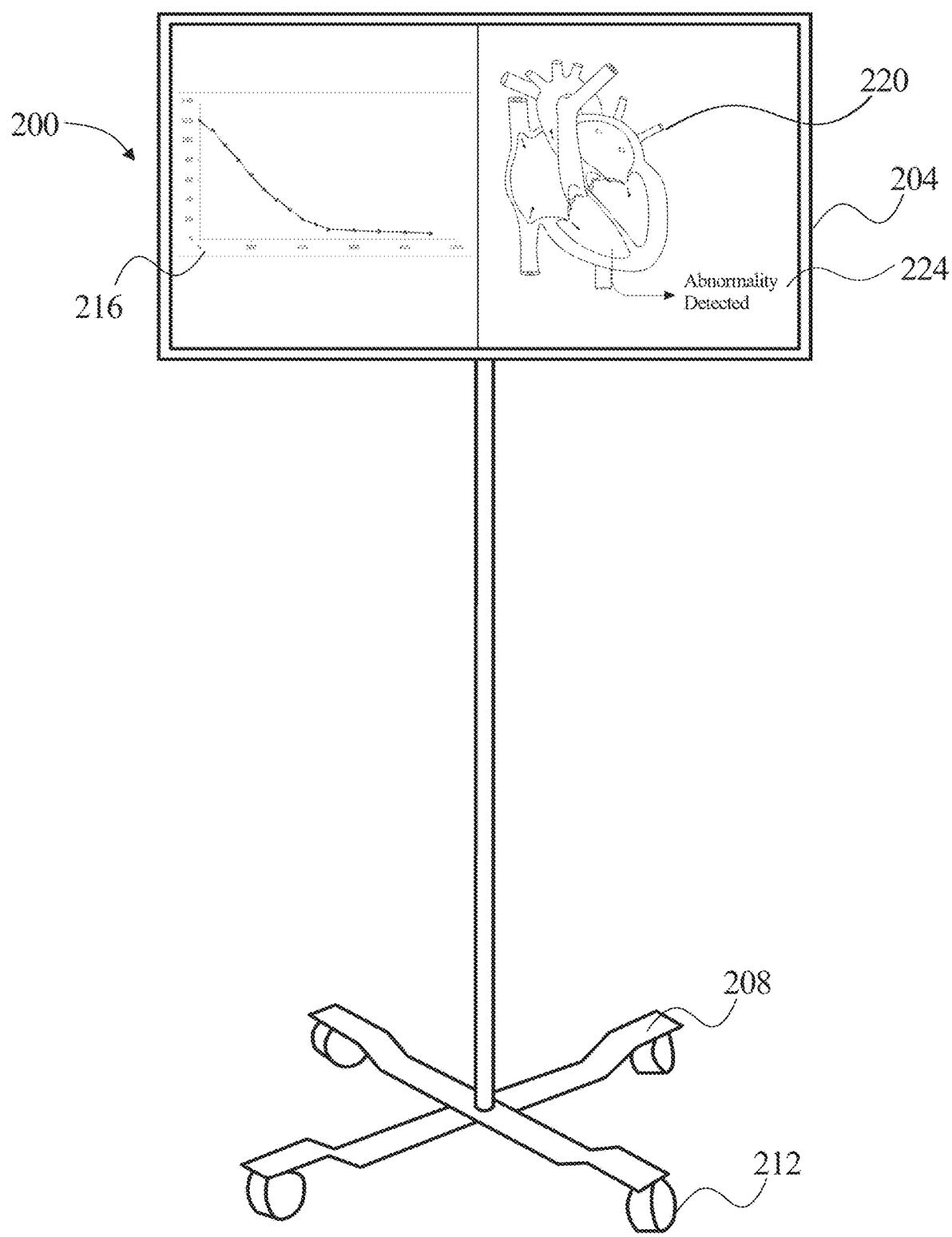
FIG. 2 is an exemplary embodiment of a mobile unit system.

With continued reference to FIG. 2, an exemplary mobile unit system 200 is described. Mobile unit system 200 may be consistent with system 100 as described in reference to FIG. 1. In one or more embodiments, mobile unit system 200 may contain a display device 204. In one or more embodiments, display device may sit atop a base 208. In one or more embodiments, base 208 may contain one or more wheels 212, and/or any other components that facilitate movement, to navigate mobile unit system 200. In one or more embodiments, mobile unit system 200 may allow for movements from one location to another. In one or more embodiments, mobile unit system 200 may allow for placement of mobile unit system 200 during particular procedures. In one or more embodiments display device 204 may be configured to display graphical visualization 216. In one or more embodiments, visualization of graphical visualization 216 may allow for medical personnel to analyze various electrical signals of a patient's heart. In one or more embodiments, graphical visualization 216 may include a two-dimensional X-Y plot wherein time may be denoted along an X axis and cardiac deviations and/or changes in ECG signals may be denoted along the Y axis. In some embodiments, for example, a distance metric of a cardiac deviation may be displayed on the X-axis. In one or more embodiments, following an ablation procedure, cardiac deviations may decrease wherein graphical visualization 216 may depict a trend line decreasing to zero. In one or more embodiments, the trend line may be used to determine if a particular abnormality had been corrected and/or if another abnormality is currently present. In one or more embodiments, cardiac deviation may contain deviations between consecutive cycles wherein changes within the consecutive cycles are plotted and determined. In one or more embodiments, graphical visualization 216 may be used to visually determine if a particular abnormality had been corrected. In one or more embodiments, graphical visualization 216 may be used to signal to a medical professional whether a particular abnormality exists. In one or more embodiments, cardiac deviations may remain relatively stagnant for short periods of time following an ablation procedure prior to decreasing. In one or more embodiments, cardiac deviations may be used to determine if a vector loop is open or closed wherein an open vector loop is associated with a cardiac deviation above zero and a closed vector loop is associated with a cardiac deviation at or close to zero. In one or more embodiments, sensors may be connected to mobile unit system 200 either through a wired connection and/or wirelessly. In one or more embodiments, mobile unit system may include computing device 104 as described in reference to FIG. 1. In one or more embodiments, display device may further be configured to display a graphical image 220. In one or more embodiments, graphical image 220 may include an image and/or diagram of a human heart. In one or more embodiments, graphical image 220 may be representative of a patient's heart. In one or more embodiments, display device may be configured to determine ablative reaction 224 such as any ablative reaction as described in reference to FIG. 1 and display them above and/or near graphical image 220. In this instance, an ablative reaction 224 may include an arrow indicating that an abnormality has been detected in a particular region of the heart. In one or more embodiments, ablative reactions 224 may include audible alerts, changes in color and/or any other indication that may be used to inform a medical professional that an issue exists. In one or more embodiments, one or more processes as described above may be performed on mobile unit system 200. In one or more embodiments, mobile unit system 200 may be communicatively connected to a cloud network wherein one or more processes may be performed by the cloud network. In some embodiments, ablative reaction may be triggered as a function of a cardiac deviation or distance metric. As a non-limiting example, ablative reaction may be triggered when cardiac deviation or distance metric exceeds a threshold value. As a non-limiting example, ablative reaction may be triggered when cardiac deviation or distance metric falls below a threshold value. As a non-limiting example, ablative reaction may be triggered when cardiac deviation or distance metric stay below a threshold value for a set amount of time or a set number of heartbeats. In some embodiments, set amount of time may be from 30 seconds to 7 minutes. In some embodiments, set amount of time may be from 1 minute to 5 minutes. In some embodiments, set amount of heat beats may be from 30 to 525 beats. In some embodiments, set amount of heat beats may be from 60 to 375 beats.

Figure 3:
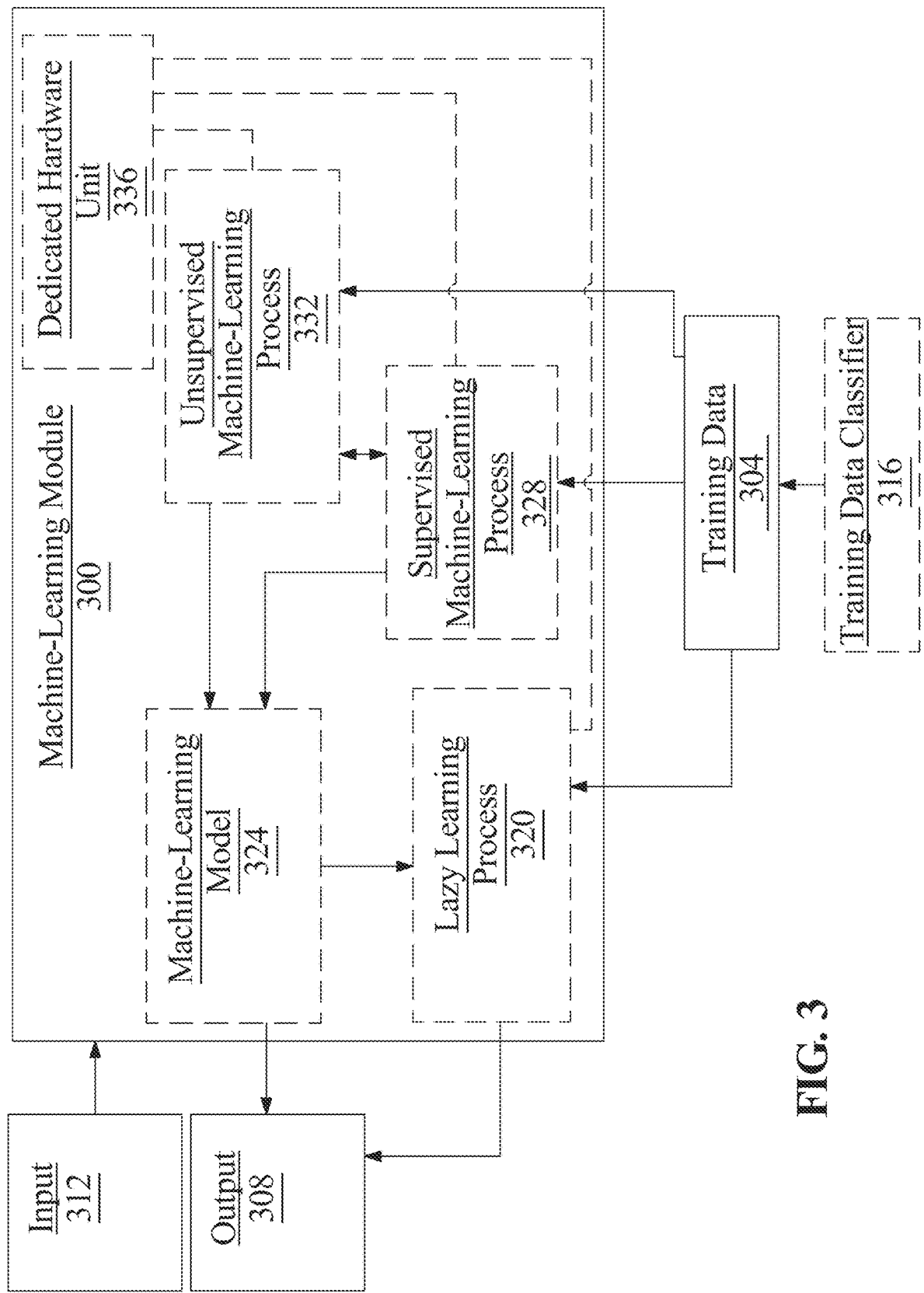
FIG. 3 is a block diagram of an exemplary machine-learning process.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example inputs may include inputs such as cardiographic image, cardiac vector, vector loops and/or any other data as described above and outputs may include outputs such as vectorcardiogram image, ablative reaction and/or any other data as described above.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to disease states, vector loops and the like. In one or more embodiments, data may first be classified to a vector loop class wherein the vector loops may include any vector loops as described above. In one or more embodiments, ablative reactions may be determined based on the classified vector loop wherein datum corresponding to one vector loop may contain differing outputs than a datum classified to another vector loop.

Still referring to FIG. 3, computing device 304 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 304 may then calculate a likelihood table by calculating probabilities of different data entries and classification labels. Computing device 304 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, computing device 304 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include vectorcardiogram image, vector loops, cardiac vector and the like as described above as inputs, ablative reaction, vector cardiogram image and the like as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
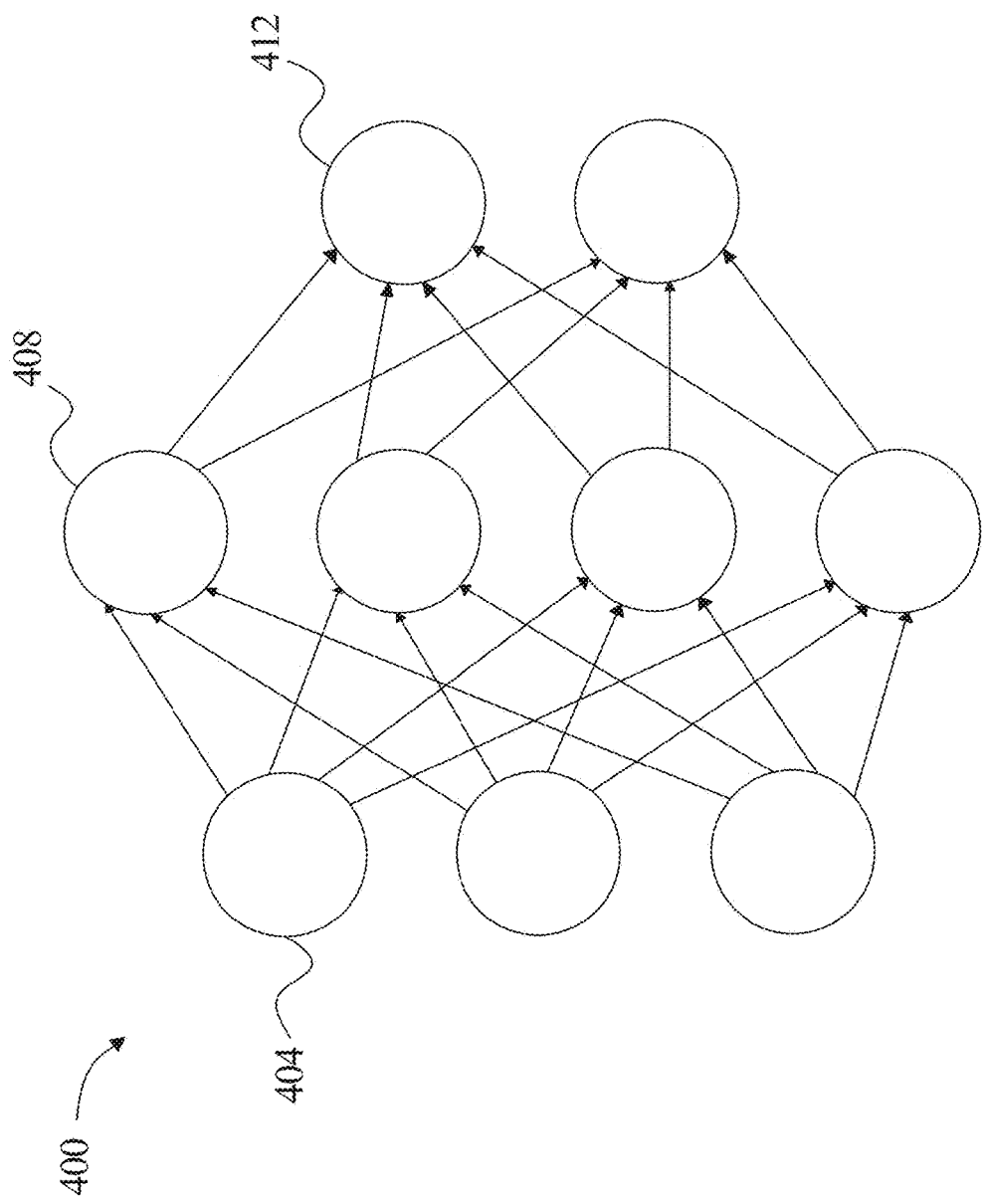
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
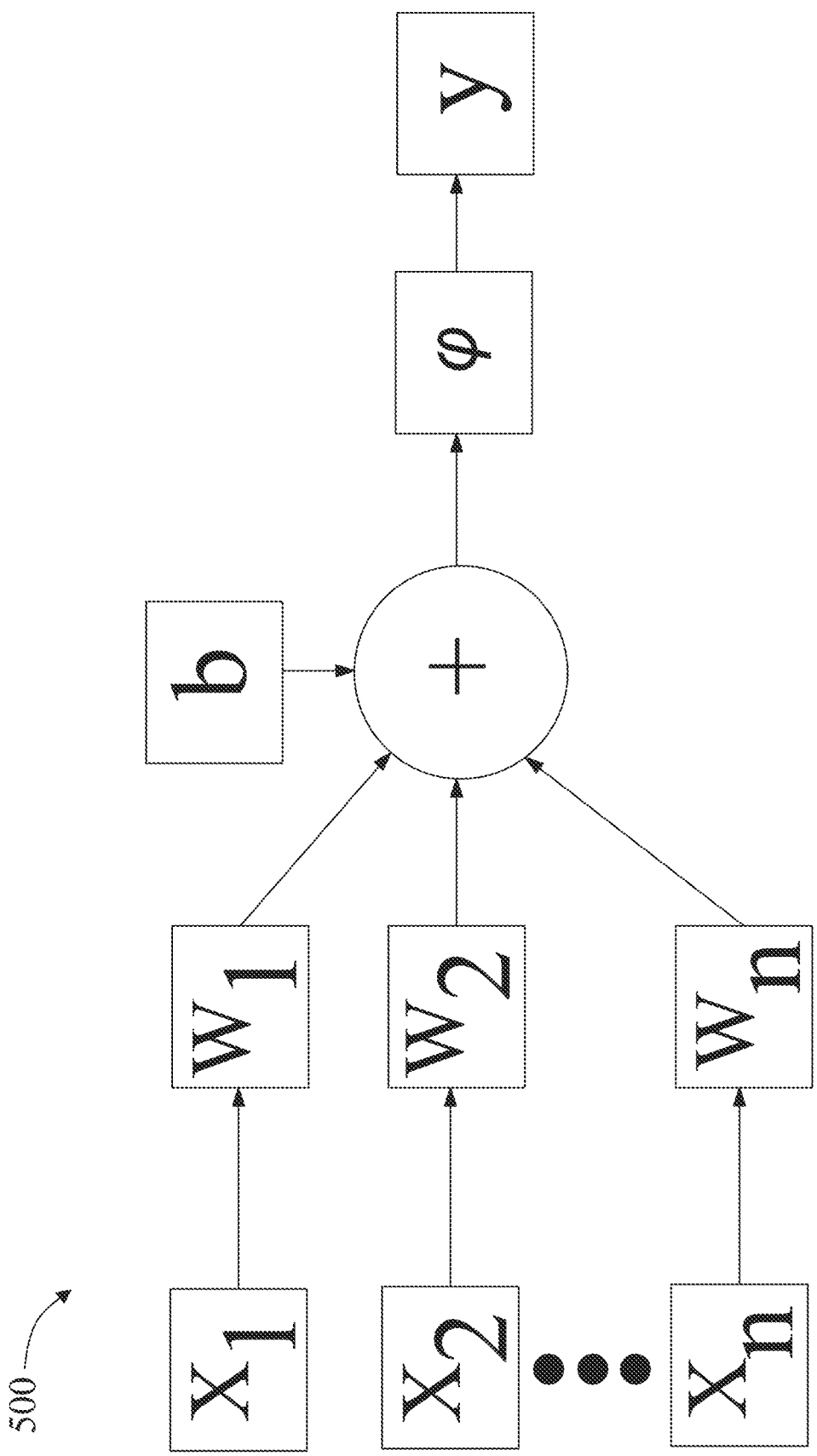
FIG. 5 is a diagram of an exemplary embodiment of a node of a neural network.

Referring now to FIG. 5, an exemplary embodiment of a node of a neural network is illustrated. A node may include, without limitation, a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
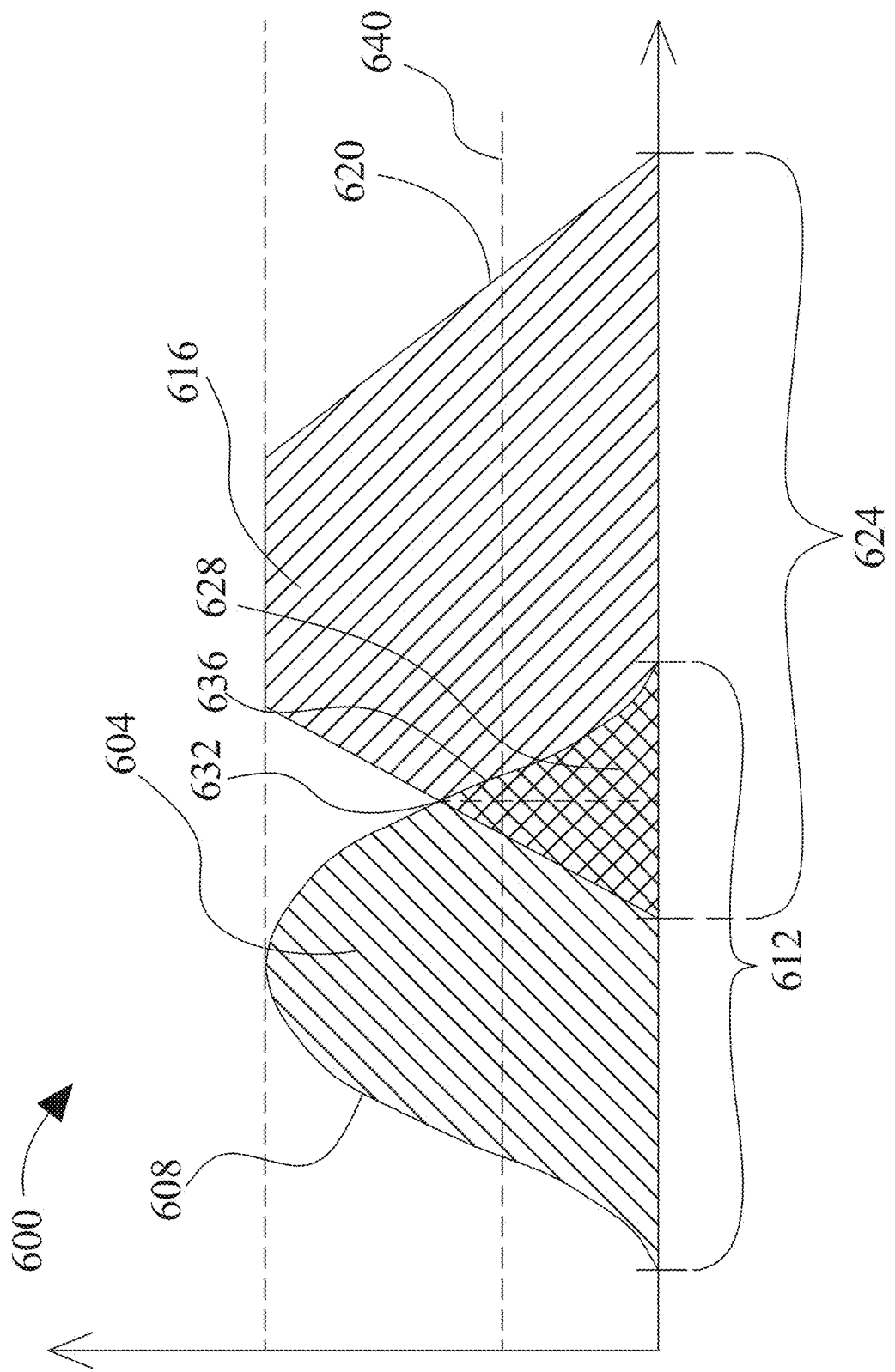
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example, and without limitation, the parameters, weights, and/or coefficients of the membership functions may be tuned using any machine-learning methods for the name/version matching as described herein. In another non-limiting embodiment, the fuzzy set may represent a vectorcardiogram image and historically vectorcardiogram image from FIG. 1.

Alternatively, or additionally, and still referring to FIG. 6, fuzzy set comparison 600 may be generated as a function of determining data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input a plurality of cardiac vectors and/or vectorcardiogram images and a plurality of historically vectorcardiogram images. For instance, an acceptance variable may represent a first measurable value pertaining to the classification of a plurality of vectorcardiogram image to an historically vectorcardiogram image. Continuing the example, an output variable may represent at least one diagnostic label. In an embodiment, a plurality of vectorcardiogram image and/or an historically vectorcardiogram image may be represented by their own fuzzy set. In other embodiments, an evaluation factor may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively, or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively, or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any a plurality of vectorcardiogram image and historically vectorcardiogram image. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616.

Alternatively, or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the assignment of at least one diagnostic label may indicate a sufficient degree of overlap with fuzzy set representing a plurality of vectorcardiogram image and an historically vectorcardiogram image for combination to occur as described above. Each threshold may be established by one or more user inputs. Alternatively, or additionally, each threshold may be tuned by a machine-learning process and/or statistical process, for instance and without limitation as described in further detail below.

In an embodiment, a degree of match between fuzzy sets may be used to rank one resource against another. For instance, if both a plurality of vectorcardiogram image and a historically vectorcardiogram image have fuzzy sets, at least one diagnostic label may be assigned by having a degree of overlap exceeding a predictive threshold, processor may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7A:
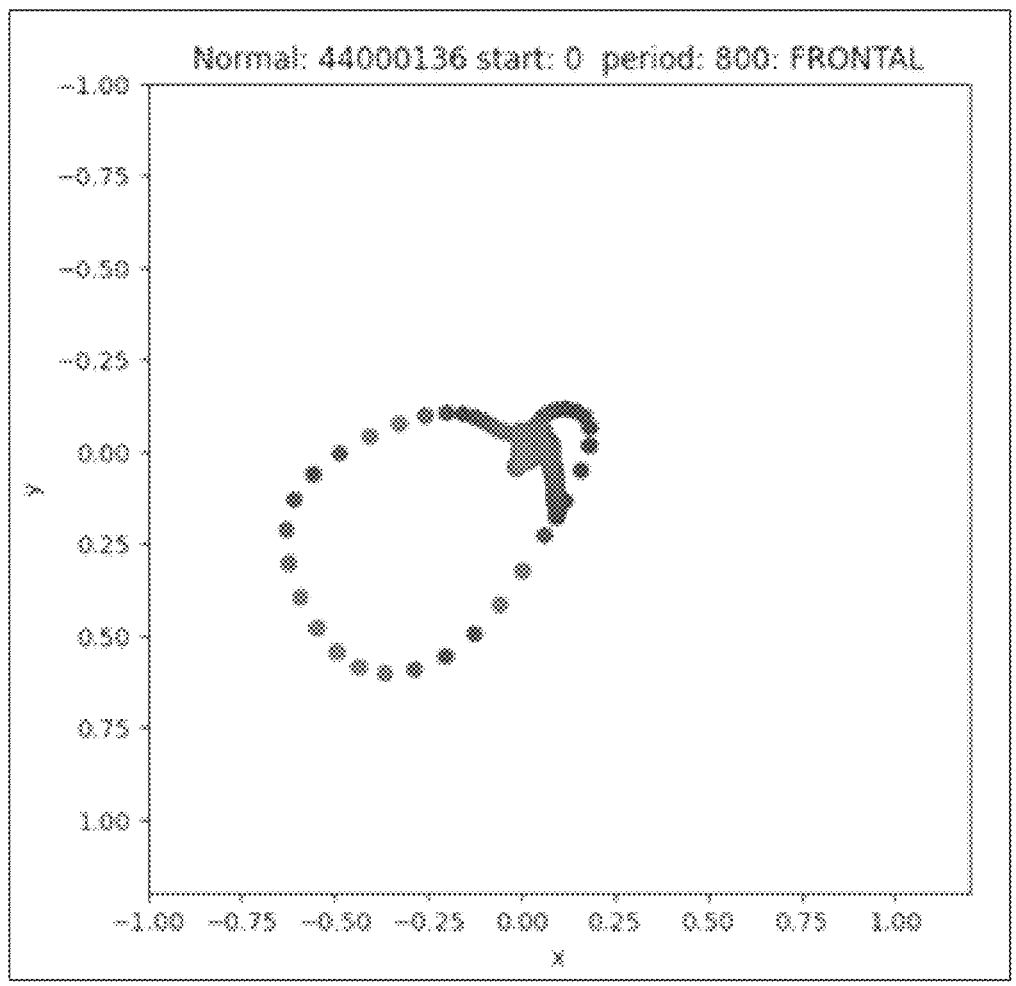
FIG. 7A is an illustration of an exemplary visualization of transformed ECG data.
Figure 7B:
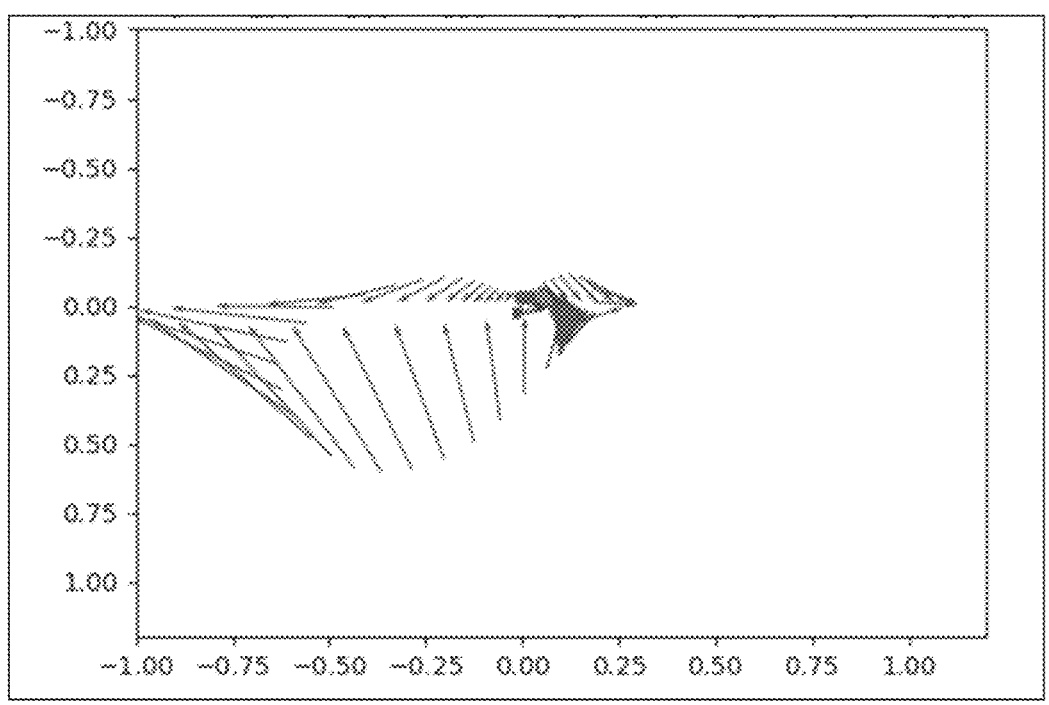
FIG. 7B is an illustration of another exemplary visualization of transformed ECG data.
Figure 7C:
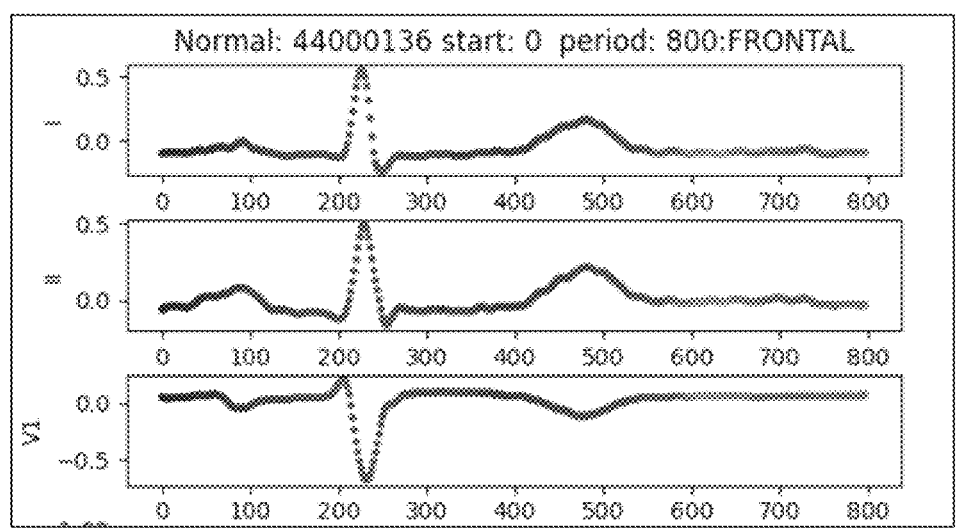
FIG. 7C is an illustration of yet another exemplary visualization of transformed ECG data.

Referring to FIGS. 7A-C, an exemplary embodiment of visualization of transformed ECGs is shown, for three overlapping time slices. In some cases, input ECGs may be a multi-lead ECG, for example a set of 12 leads; alternatively input ECG may include a subset of lead signals, e.g., a single lead ECG. An exemplary input ECG may include 5000 samples (e.g., 500 Hz sampling for 10 seconds) of 8 leads (5000×8). Input ECG may be transformed by an appropriately dimensioned matrix. For instance, an exemplary 5000-sample 8-lead (5000×8) input ECG may be transformed by a matrix of dimension 8×3 yielding a 5000×3 matrix. Generally, there is no constraint on transformation used. However, transformed vectors advantageous for visualization and further processing (e.g., feature detection) may be smooth along time axis and representative of key characteristics that aid in normal and disease fear true detection. In some cases, there is no constraint on reduction of dimension (i.e., size) of ECG data (e.g., number of leads), while preserving time axis during transformation. In some cases, transformation to an output ECG of two or three dimensions facilitates visual interpretation.

With continued reference to FIGS. 7A-C, transformed ECG may be shown. Visualization of transformed ECG may be presented by way of vector projections. For instance, vector projections of transformed ECG may be rendered in certain planes. FIGS. 7A-B illustrate a vector projection of transformed ECG in an orthogonal plane. In some cases, orthogonal plane may include any plane described in this disclosure, for example without limitation sagittal, transverse, and frontal.

Figure 8:
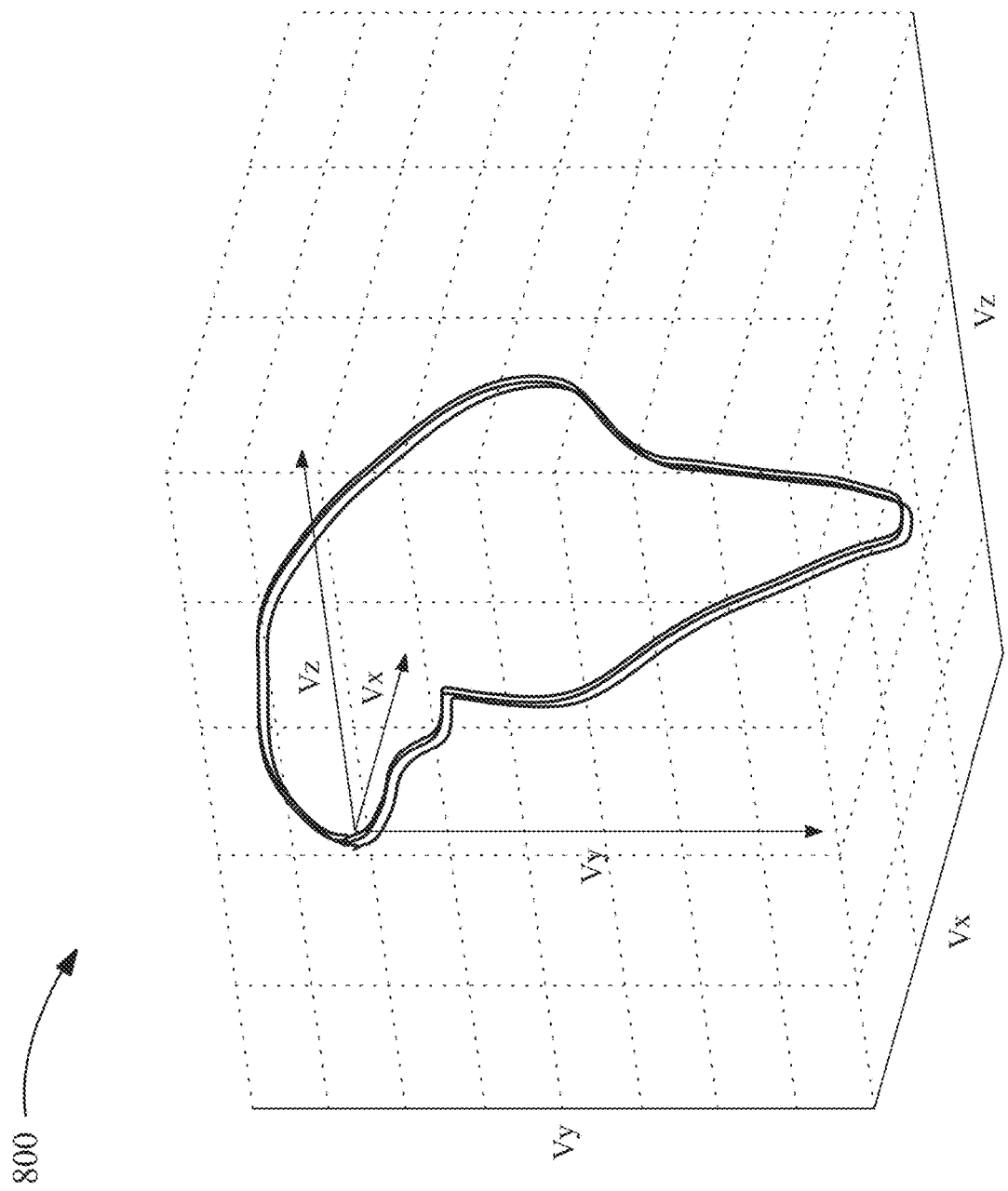
FIG. 8 is an illustration of an exemplary embodiment of vectorcardiogram image.

In FIG. 7A, each vector is shown rendered at a head position of the vector from an origin. In some cases, this rendering is similar to rendering all vectors positioned at origin. Head position rendering, in some instances, benefits human interpretation. Alternatively or additionally, head of vectors may be plotted alone with each corresponding vector rooted at origin. In FIG. 7B, each vector is shown rendered as a vector field, showing both magnitude and direction. Referring to FIGS. 7A-B, in some cases, visualized vectors might be shown terminating at vector loop, describing location of loop points. Alternatively or additionally, as shown in FIG. 8 below, origin of vector may be located at vector loop, suggesting the vectors describe a tangent envelope to the loop (e.g., velocity vectors).

Referring again to FIGS. 7A-C, visualizations for a specific projection may be rendered contiguous across time slices, having characteristics that are easily interpretable compared to corresponding ECG rendition. In some cases, renditions of contiguous time slices may be transformed into a video. Evolution of spatial representation shape of each time slice over time may reduce cognitive overload of feature extraction by humans and improve detectability of anomalies that are spread across both a single lead and multiple leads collectively over time.

FIG. 7C illustrates two dimensional representations of each dimension of a three-dimensional transformed ECG, with amplitude shown along a vertical axis and time shown along a horizontal axis. Visualizations according to that shown in FIG. 7C may show transformed ECG in sagittal, transverse, and frontal planes. Visualizations according to that shown in FIG. 7C may show transformed ECG over one or more heart cycles. In one or more embodiments, visualizations may include representation wherein time may be represented along an X-axis and distances may be represented along a Y-axis. In one or more embodiments, visualization may be used to determine ablative reactions as described above in reference to FIG. 1. In one or more embodiments, a computing device such as one described in reference to FIG. 1, may be configured to generate visualizations wherein the visualizations may indicate various cardiac abnormalities.

Referring again to FIGS. 7A-C, in some cases, visualizations may enable machine learning processes that use transformed ECGs and/or visualizations of transformed ECGs as inputs. Machine learning processes may include any machine learning process described in this disclosure. Exemplary machine learning process may include feature detectors, such as for scale invariant feature transform (SIFT), Canny edge detection, Shi Tomasi corner detection, and the like. In some cases. For example, in some embodiments visualization of transformed ECGs, like those shown in FIGS. 7A-C, may be input to image classifiers (e.g., supervised training or self-supervised learning), with or without an intervening feature detection step. In some cases, visualizations of transformed ECGs may be used as input to a machine learning processes paired with corresponding text.

Referring now to FIG. 8, is another illustration of an exemplary embodiment of vectorcardiogram image 800. The display device may display the vectorcardiogram image 800 in a graphical format to facilitate visual comparison. In some cases, the vectorcardiogram images 800 can be overlaid on top of each other or displayed side by side for visual inspection and assessment of similarities or differences. Graphical representations, such as vector loops or waveform plots, can be used to aid in the comparison. In some cases, the display device may display the vectorcardiogram image 800 in an annotated format along with diagnostic features and diagnostic labels. The vectorcardiogram image 800 provides valuable insights into the cardiac vector's magnitude and direction during the cardiac cycle. In a vectorcardiogram image 800, several diagnostic features can be identified. The loop shape and size are indicative of the overall cardiac performance. Axis deviation, represented by the angle of the loop, can suggest abnormalities such as left ventricular hypertrophy or right ventricular strain. Loop rotation can reveal bundle branch blocks or ventricular tachycardia. The spatial distribution of electrical vectors helps assess chamber enlargement or myocardial infarction location. Each of these diagnostic features may be associated with one or more diagnostic labels. Diagnostic labels associated with the vectorcardiogram image 800 may include normal sinus rhythm, atrial fibrillation, myocardial ischemia, ventricular hypertrophy, and bundle branch blocks. Analyzing diagnostic features and diagnostic labels in a vectorcardiogram image 800 aids in diagnosing various cardiac conditions and guiding appropriate treatment strategies.

Figure 9:
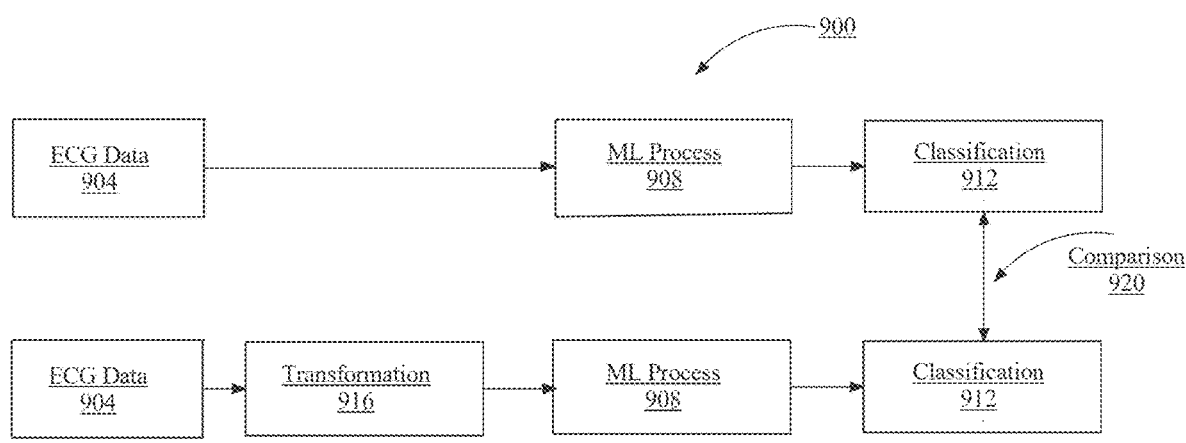
FIG. 9 is a block diagram of an exemplary method for comparing diagnostic processes.

Referring now to FIG. 9, a block diagram represents an exemplary system 900 for comparing usefulness of ECG transformation in classification. System 900 may receive ECG data 904. ECG data 904 may include 12-lead ECGs. System 900 may perform machine learning processes 908 and classification 912 on ECG data 904. Machine learning processes 908 and classification 912 may include any machine learning processes, models, classifiers, and the like described in this disclosure. System 900 may additionally transform 916 ECG data. For instances and without limitation, system 900 may transform 916 ECG data into a vectorcardiogram. System 900 may use comparable machine learning processes 908 and classify 912 transformed ECG data. For instance, system may use a transformer model to classify the resultant vector representation by heart condition. System 900 may compare 920 classification 912 with raw ECG data and transformed data 916. In some cases, transformation 916 of ECG data enables improved classification. Table below shows improved classification using transformed ECG.

| Transformation: | No transformation | VCG transformation |
|---|---|---|
| RBBB | [AUC +/− CI] | [AUC +/− CI] |
| LBBB | [AUC +/− CI] | [AUC +/− CI] |
| LAFB | [AUC +/− CI] | [AUC +/− CI] |
| PH | [AUC +/− CI] | [AUC +/− CI] |
| LPFB | [AUC +/− CI] | [AUC +/− CI] |
| Trifascicular | [AUC +/− CI] | [AUC +/− CI] |
| First degree AV | [AUC +/− CI] | [AUC +/− CI] |
| LVEF | [AUC +/− CI] | [AUC +/− CI] |

Figure 10:
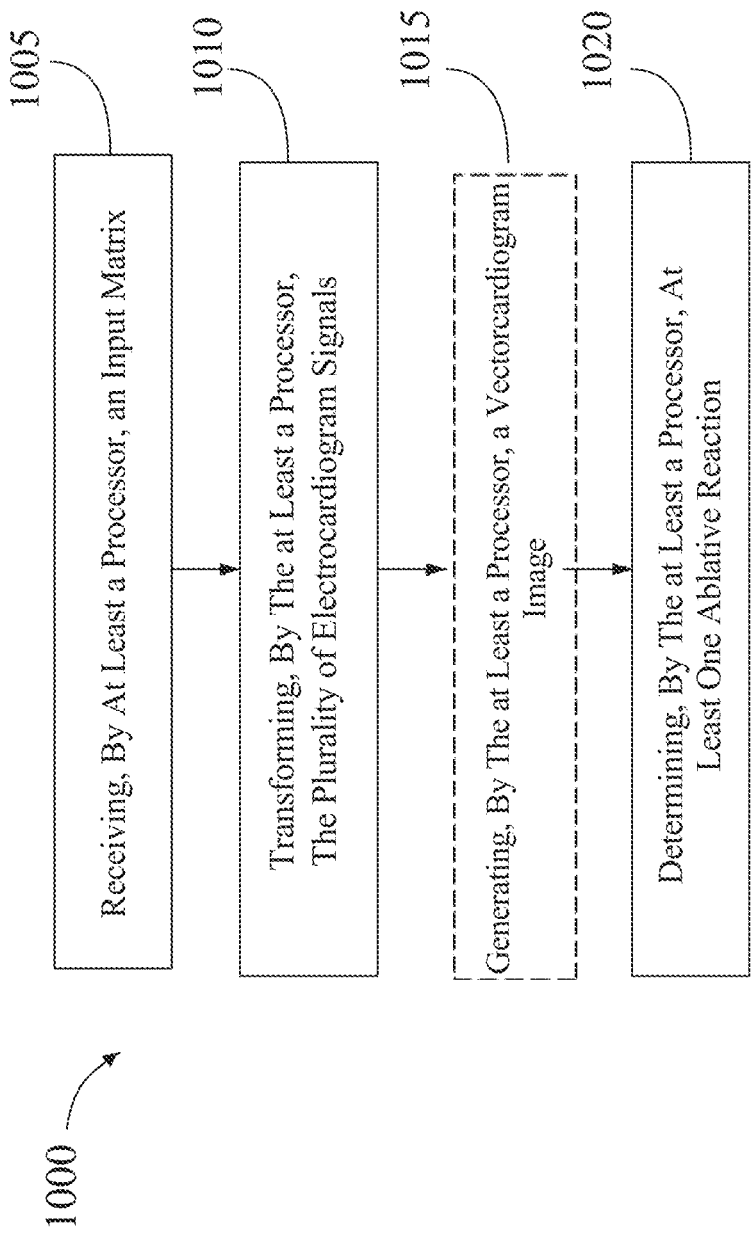
FIG. 10 is a flow diagram of an exemplary system for visualization of vectorcardiograms for ablation procedures.

Referring now to FIG. 10, an exemplary method 1000 for visualization of vectorcardiograms for ablation procedures is described. At step 1005, method 1000 includes receiving, by at least a processor, an input matrix comprising a plurality of electrocardiogram signals associated with a plurality of time variables, wherein the plurality of electrocardiogram signals is generated using at least one sensor of a plurality of sensors connected to a patient during an ablation procedure. In one or more embodiments, the plurality of electrocardiogram signals are associated with a 12-lead electrocardiogram. This may be implemented with reference to FIGS. 1-10 and without limitation.

With continued reference to FIG. 10, at step 1010, method 1000 includes transforming, by the at least a processor, the plurality of electrocardiogram signals into a cardiac vector as a function of the input matrix. This may be implemented with reference to FIGS. 1-10 and without limitation.

With continued reference to FIG. 10, at step 1015 method 1000 may include generating, by the at least a processor, a vectorcardiogram image as a function of the cardiac vector, wherein the vectorcardiogram image comprises a representation of the cardiac vector in a three-dimensional (3D) space. This may be implemented with reference to FIGS. 1-10 and without limitation.

With continued reference to FIG. 10, at step 1020 method 1000 may include determining, by the at least a processor, at least one ablative reaction for the vectorcardiogram image. In one or more embodiments, step 1020 may include determining, by the at least a processor, at least one ablative reaction as a function of the cardiac vector, wherein determining the at least one ablative reaction includes generating a graphical visualization of an X-Y plot, wherein cardiac deviations are plotted along a vertical axis of the X-Y plot and time variables are plotted along a horizontal axis of the X-Y plot. In one or more embodiments, cardiac deviation may include a change in cardiac cycles. In one or more embodiments, cardiac deviation includes a change in magnitude between the cardiac vector at the start of a cardiac cycle and the cardiac vector at the end of a cardiac cycle. In one or more embodiments, cardiac deviation includes a Euclidean distance between two cardiac vectors at successive time intervals. In one or more embodiments, the at least one ablative reaction includes an audible alert. In one or more embodiments, determining, by the at least a processor, the at least one ablative reaction includes retrieving a plurality of historical vectorcardiogram images and determining the at least one ablative reaction as a function of a comparison between the vectorcardiogram image and the plurality of historical vectorcardiogram images. In one or more embodiments, the at least one ablative reaction includes information associated with one or more abnormal conduction pathways. In one or more embodiments, determining the at least one ablative reaction includes determining a diagnostic label as a function of the vectorcardiogram image. In one or more embodiments, determining at least one ablative reaction includes receiving a cardiographic training data having a plurality of vector cardiogram images correlated to a plurality of ablative reactions, training a cardiographic machine learning model as a function of the cardiographic training data and determining at least one ablative reaction as a function of the vectorcardiogram image and the cardiographic machine learning model. In one or more embodiments, method 1000 may further include iteratively training, by the at least a processor, the cardiographic machine learning model as a function of a user input and the vectorcardiogram image. In one or more embodiments, the vectorcardiogram image includes one or more vector loops and determining, by the at least a processor, the at least one ablative reaction for the vectorcardiogram image includes assigning an ablative color to each of the one on one or more vector loops. In one or more embodiments, determining, by the at least a processor, the at least one ablative reaction as a function of the vectorcardiogram image includes localizing an abnormality to at least one heart chamber and determining the at least one ablative reaction as a function of the localized abnormality. This may be implemented with reference to FIGS. 1-10 and without limits It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
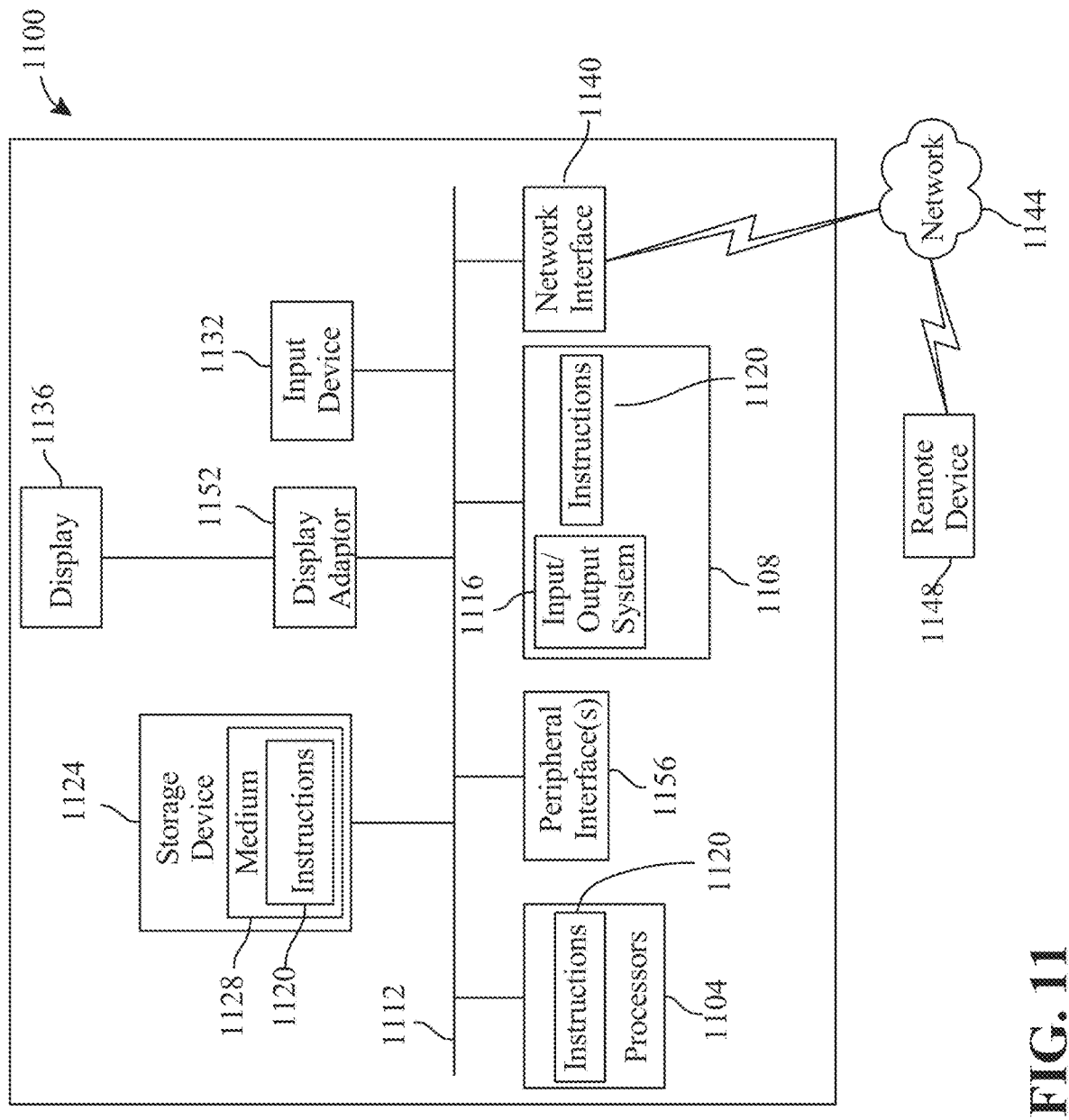
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for visualization of vectorcardiograms for ablation procedures, the system comprising:
   a processor; and
   a memory communicatively connected to the processor, the memory containing instructions configuring the processor to:
   receive an input matrix comprising a plurality of electrocardiogram signals associated with a plurality of time variables, wherein the plurality of electrocardiogram signals are generated using at least one sensor of a plurality of sensors connected to a patient during an ablation procedure;
   transform the plurality of electrocardiogram signals into a cardiac vector as a function of the input matrix;
   determine at least one ablative reaction as a function of the cardiac vector, wherein determining the at least one ablative reaction comprises generating a graphical visualization of an X-Y plot, wherein cardiac deviations are plotted along a vertical axis of the X-Y plot and time variables are plotted along a horizontal axis of the X-Y plot, wherein determining the at least one ablative reaction comprises:
   generating a vectorcardiogram image as a function of the cardiac vector;
   training, iteratively, a cardiographic machine learning model as a function of cardiographic training data and a user input, wherein:
   the cardiographic training data comprises a plurality of vector cardiogram images correlated to a plurality of ablative reactions; and
   the user input comprises a correction to one or more ablative reactions of the plurality of ablative reactions; and
   determining the at least one ablative reaction as a function of the vectorcardiogram image using the trained cardiographic machine learning model; and
   determine a new heart abnormality that occurred during the ablation procedure based on the at least one ablative reaction.

2. The system of claim 1, wherein the at least one ablative reaction comprises an audible alert.

3. The system of claim 1, wherein the cardiac deviation comprises a Euclidean distance between two cardiac vectors at successive time intervals.

4. The system of claim 1, wherein the at least one ablative reaction further comprises information associated with one or more abnormal conduction pathways.

5. The system of claim 1, wherein:
   the vectorcardiogram image comprises a representation of the cardiac vector in a three-dimensional (3D) space; and
   determining the at least one ablative reaction comprises determining a diagnostic label as a function of the vectorcardiogram image.

6. The system of claim 1, wherein:
   the vectorcardiogram image comprises one or more vector loops; and
   determining the at least one ablative reaction for the vectorcardiogram image comprises assigning an ablative color to each of the one on one or more vector loops.

7. The system of claim 1, wherein determining the at least one ablative reaction comprises:
   localizing an abnormality to at least one heart chamber;
   determining the at least one ablative reaction as a function of the localized abnormality.

8. The system of claim 1, wherein the plurality of electrocardiogram signals are associated with a 12-lead electrocardiogram.

9. A method for visualization of vectorcardiograms for ablation procedures, the method comprising:
   receiving, by a processor, an input matrix comprising a plurality of electrocardiogram signals associated with a plurality of time variables, wherein the plurality of electrocardiogram signals are generated using at least one sensor of a plurality of sensors connected to a patient during an ablation procedure;
   transforming, by the processor, the plurality of electrocardiogram signals into a cardiac vector as a function of the input matrix;
   determining, by the processor, at least one ablative reaction as a function of the cardiac vector, wherein determining the at least one ablative reaction comprises generating a graphical visualization of an X-Y plot, wherein cardiac deviations are plotted along a vertical axis of the X-Y plot and time variables are plotted along a horizontal axis of the X-Y plot, wherein determining the at least one ablative reaction comprises:
   generating a vectorcardiogram image as a function of the cardiac vector;
   training, iteratively, a cardiographic machine learning model as a function of cardiographic training data and a user input, wherein:
   the cardiographic training data comprises a plurality of vector cardiogram images correlated to a plurality of ablative reactions; and
   the user input comprises a correction to one or more ablative reactions of the plurality of ablative reactions; and
   determining the at least one ablative reaction as a function of the vectorcardiogram image using the trained cardiographic machine learning model; and
   determining, by the processor, a new heart abnormality that occurred during the ablation procedure based on the at least one ablative reaction.

10. The method of claim 9, wherein the at least one ablative reaction comprises an audible alert.

11. The method of claim 9, wherein the cardiac deviation comprises a Euclidean distance between two cardiac vectors at successive time intervals.

12. The method of claim 9, wherein the at least one ablative reaction comprises information associated with one or more abnormal conduction pathways.

13. The method of claim 9, wherein:
   the vectorcardiogram image comprises a representation of the cardiac vector in a three-dimensional (3D) space; and
   determining, by the processor, the at least one ablative reaction comprises determining a diagnostic label as a function of the vectorcardiogram image.

14. The method of claim 9, wherein:
   the processor is further configured to generate a vectorcardiogram image as a function of the cardiac vector, wherein the vectorcardiogram image comprises a representation of the cardiac vector in a three-dimensional (3D) space;
   the vectorcardiogram image comprises one or more vector loops; and determining, by the processor, the at least one ablative reaction for the vectorcardiogram image comprises assigning an ablative color to each of the one on one or more vector loops.

15. The method of claim 9, wherein determining, by the processor, the at least one ablative reaction comprises:
 localizing an abnormality to at least one heart chamber;
 determining the at least one ablative reaction as a function of the localized abnormality.

16. The method of claim 9, wherein the plurality of electrocardiogram signals are associated with a 12-lead electrocardiogram.

* * * * *